(12) United States Patent
Roddy et al.

(10) Patent No.: US 11,826,537 B2
(45) Date of Patent: Nov. 28, 2023

(54) MEDICAL TUBING ORGANIZER

(71) Applicants: UWM Research Foundation, Inc., Milwaukee, WI (US); RoddyMedical, LLC, Wauwatosa, WI (US)

(72) Inventors: Lindsey Roddy, Wauwatosa, WI (US); Kyle S. Jansson, Wauwatosa, WI (US)

(73) Assignees: UWM Research Foundation, Milwaukee, WI (US); RoddyMedical, LLC, Wauwatosa, WI (US)

( * ) Notice: Subject to any disclaimer, the term of this patent is extended or adjusted under 35 U.S.C. 154(b) by 650 days.

(21) Appl. No.: 15/878,147

(22) Filed: Jan. 23, 2018

(65) Prior Publication Data

US 2018/0207416 A1 Jul. 26, 2018

Related U.S. Application Data

(60) Provisional application No. 62/449,360, filed on Jan. 23, 2017.

(51) Int. Cl.
*A61M 39/08* (2006.01)
*A61M 39/24* (2006.01)
(Continued)

(52) U.S. Cl.
CPC .......... *A61M 39/08* (2013.01); *A61M 5/1415* (2013.01); *A61M 5/1418* (2013.01);
(Continued)

(58) Field of Classification Search
CPC .. A61M 39/08; A61M 5/1415; A61M 5/1418; A61M 25/02; A61M 39/24
(Continued)

(56) References Cited

U.S. PATENT DOCUMENTS 3,630,195 A 12/1971 Santomieri
3,696,920 A * 10/1972 Lahay .................... A61B 50/30
206/370

(Continued)

OTHER PUBLICATIONS

Strip T's, "Sterile Adhesive Organizer," <https://www.kappsurgical.com/wp-content/uploads/2016/12/Kapp-Strip-Ts-FFS_2pg_for-web_pdf> webpage publicly available at least as early as Jun. 11, 2019.
(Continued)

*Primary Examiner* — Terrell L McKinnon
*Assistant Examiner* — Michael McDuffie
(74) *Attorney, Agent, or Firm* — Quarles & Brady LLP

(57) ABSTRACT

A medical tubing organizer includes a base defining a longitudinal direction, a lateral direction being defined as substantially orthogonal to the longitudinal direction, and a vertical direction being defined as substantially orthogonal to the longitudinal and lateral directions. A tube retainer is positioned on a top of the base and configured to receive a medical tube that extends along the lateral direction. The tube retainer is further configured to adjust between a free flow state and a retention state, wherein, in the free flow state, the tube retainer is configured to enable movement of the medical tube in the lateral direction and resist movement in the longitudinal direction, and in the retention state, the tube retainer is configured to resist movement in the lateral, longitudinal, and vertical directions. A connector is positioned on the base for selectively coupling the medical tubing organizer to a structure.

24 Claims, 20 Drawing Sheets

(51) Int. Cl.
   *A61M 25/02* (2006.01)
   *A61M 5/14* (2006.01)
(52) U.S. Cl.
   CPC ............ *A61M 25/02* (2013.01); *A61M 39/24* (2013.01); *A61M 2005/1416* (2013.01); *A61M 2025/024* (2013.01); *A61M 2025/026* (2013.01); *A61M 2025/0213* (2013.01); *A61M 2209/084* (2013.01)
(58) Field of Classification Search
   USPC ... 248/690, 49, 58, 60, 62, 65, 68.1, 69, 70, 248/73, 74.1, 74.3; 604/174
   See application file for complete search history.

(56) References Cited

U.S. PATENT DOCUMENTS

| | | | | |
|---|---|---|---|---|
| 4,606,735 | A | 8/1986 | Wilder et al. | |
| 4,759,963 | A * | 7/1988 | Uso, Jr. | A01K 97/08 224/901.4 |
| 4,846,816 | A * | 7/1989 | Manfredi | A61F 5/4405 604/323 |
| 4,896,465 | A * | 1/1990 | Rhodes | A61M 5/1418 128/849 |
| 4,971,271 | A * | 11/1990 | Sularz | A61M 5/1418 248/229.13 |
| 5,084,026 | A * | 1/1992 | Shapiro | A61M 25/02 128/DIG. 15 |
| 5,188,319 | A * | 2/1993 | Hawash | F16L 3/23 248/68.1 |
| 5,224,674 | A * | 7/1993 | Simons | F16L 3/2235 248/68.1 |
| 5,237,769 | A * | 8/1993 | Navarro | A01K 97/12 248/538 |
| 5,316,246 | A | 5/1994 | Scott et al. | |
| 5,334,186 | A | 8/1994 | Alexander | |
| 5,336,179 | A | 8/1994 | Ryan | |
| 5,389,082 | A * | 2/1995 | Baugues | A61M 5/1418 128/DIG. 26 |
| 5,535,928 | A * | 7/1996 | Herring | A45F 5/021 224/901 |
| 5,558,440 | A * | 9/1996 | Miller | A45C 1/04 224/219 |
| 5,876,371 | A | 3/1999 | Yokoyama et al. | |
| 6,382,568 | B1 | 5/2002 | Snell | |
| 6,458,104 | B2 | 10/2002 | Gautsche | |
| D479,328 | S | 9/2003 | Reynolds et al. | |
| 6,843,399 | B2 * | 1/2005 | Garcia | F42B 39/02 224/665 |
| 7,062,822 | B2 * | 6/2006 | Folkmar | A44B 99/00 24/30.5 R |
| 7,284,729 | B2 * | 10/2007 | Walsh | A61M 25/02 128/877 |
| 7,284,730 | B2 * | 10/2007 | Walsh | A61M 25/02 128/877 |
| 7,320,681 | B2 | 1/2008 | Gillis et al. | |
| 7,457,506 | B1 * | 11/2008 | Osborne, II | F16L 3/2235 248/68.1 |
| 8,020,825 | B2 | 9/2011 | Dostaler et al. | |
| 8,038,104 | B1 * | 10/2011 | Larkin | H02G 3/32 248/55 |
| 8,371,000 | B1 * | 2/2013 | Schultz | B65D 63/10 24/306 |
| 8,998,151 | B2 * | 4/2015 | Hoek | H02G 3/32 248/68.1 |
| 9,386,824 | B1 * | 7/2016 | Schultz | A44B 18/0019 |
| 9,638,354 | B1 * | 5/2017 | Ogueli | A61M 5/1418 |
| 10,583,243 | B2 * | 3/2020 | Burke | A61M 25/02 |
| 2003/0132352 | A1 * | 7/2003 | Weaver | F16L 3/223 248/68.1 |
| 2004/0118982 | A1 | 6/2004 | Shillings et al. | |
| 2005/0077436 | A1 | 4/2005 | Nelson | |
| 2005/0273987 | A1 * | 12/2005 | Honchel | A61B 90/50 24/442 |
| 2006/0113432 | A1 | 6/2006 | Driskell | |
| 2006/0237597 | A1 * | 10/2006 | D'Andria | F16L 3/223 248/68.1 |
| 2007/0114339 | A1 * | 5/2007 | Winchester | F16L 3/223 248/68.1 |
| 2007/0142785 | A1 * | 6/2007 | Lundgaard | F16L 3/223 604/179 |
| 2007/0282272 | A1 * | 12/2007 | Bannon | A61M 5/1418 604/174 |
| 2009/0065249 | A1 * | 3/2009 | Silvers | H02G 3/30 174/72 A |
| 2011/0054409 | A1 * | 3/2011 | Nishtala | A61M 25/02 604/179 |
| 2011/0147542 | A1 * | 6/2011 | Hoek | F16L 3/223 248/68.1 |
| 2012/0277682 | A1 * | 11/2012 | Corato | A61M 25/02 604/179 |
| 2013/0138044 | A1 | 5/2013 | Schuman et al. | |
| 2014/0252177 | A1 | 9/2014 | Vera | |
| 2015/0129726 | A1 * | 5/2015 | Sherman | H02G 3/30 248/68.1 |
| 2015/0141962 | A1 | 5/2015 | Collins et al. | |

OTHER PUBLICATIONS

Surge Cardiovascular, "Tubing Organizers," <https://surgecardiovascularcom/product/tubing-organizers/> website accessed Apr. 14, 2019.
Haynes, et al., Managing Spaghetti Syndrome in Critical Care With a Novel Device: A Nursing Perspective, Critical Care Nurse, vol. 35, No. 6, pp. 38-45, Dec. 2015.
Xodus Medical, Inc., "Tube Holder Brochure," <https://web.archive.org/web/20101206190840/http://www.xodusmedical.com/downloads/Brochures/Tube-Holder.pdf> publicly available at least as early as Dec. 11, 2013.
NovoSci, "Pediatric Tubing Organizer," <http://www.s127139381.onlinehome.us/Media/sales_sheets/Pediatric_Tubing_Organizer.pdf> website accessed May 2017.
The Beata Clasp, "Tubing, Line, and Drain Organizer," <http://www.beataclasp.com/Product.htm>, publicly available at least as early as Nov. 20, 2008.
IVA, "IV Organization System," <https://www.behance.net/gallery/51967161/IVA>, website accessed Jan. 2018.
DaVinci Medical, "IV Guard," <https://mcarthurmedical.com/sites/default/files/IV%20Guard%20Brochure%20IVG032016%20HiRes(1)%20MMSI(1)_0.pdf>, publicly available at least as early as Aug. 8, 2018.
NewMediaWire, "Introducing the Perfect Gift for Nurses On Certified Nurses Day: The Easy View IV Tube Separator!," <http://www.newmediawire.com/news/introducing-the-perfect-gift-for-nurses-on-certified-nurses-day:-the-easy-view-iv-tube-separator-3090182 >, publicly available at least as early as Mar. 10, 2014.
Healthcare Logistics Inc., "IV Line Holder," <https://www.youtube.com/watch?v=u0X8jnW9GrM&t=1s>, publicly available at least as early as Mar. 15, 2016.
JMC Global Technologies, "JanaBand," <https://www.janaband.net>, publicly available at least as early as Oct. 11, 2011.
IV Organizer, "The IV Tube Organizer," <https://ivorganizer.com/> publicly available at least as early as Oct. 16, 2013.
"Nurse Buddy Multiple IV Line Organizer Patent Pending USPTO," <https://www.youtube.com/watch?v=T2GMDSq5sh8> publicly available at least as early as Sep. 27, 2012.
MarketLab, "IV Line Holder," <https://www.marketlab.com/iv-line-holder/p/IVLineHolder/> publicly available at least as early as Jun. 12, 2015.

* cited by examiner

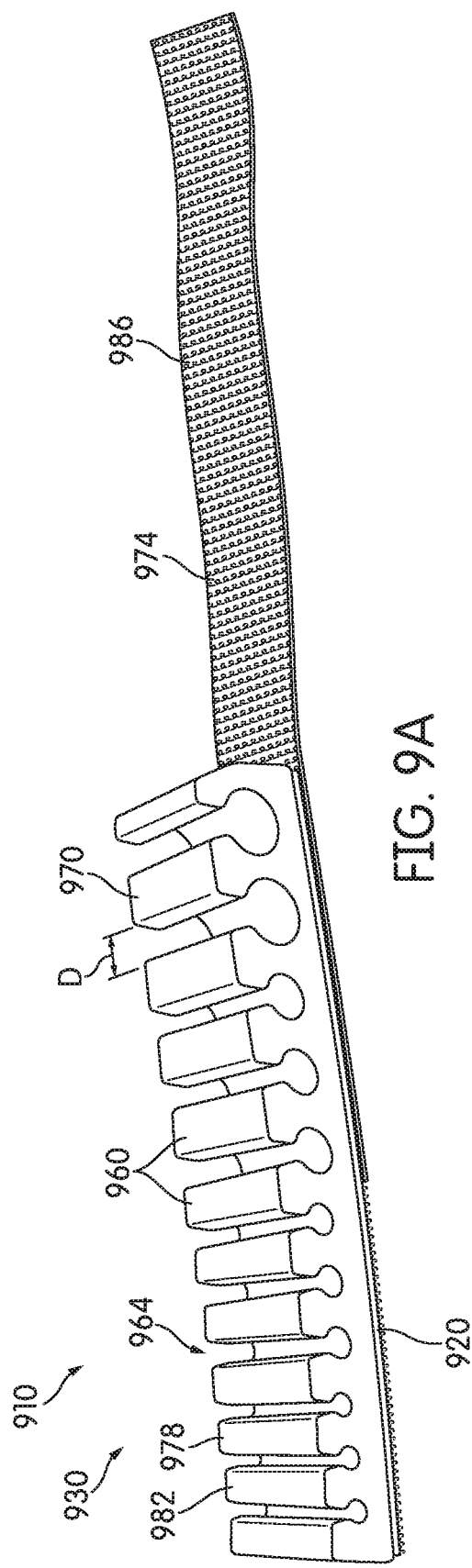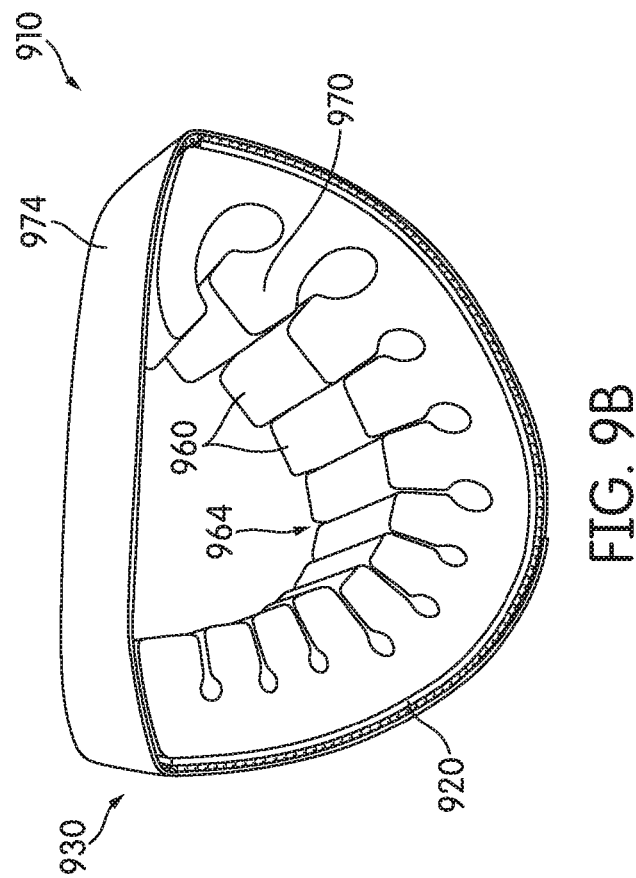

MEDICAL TUBING ORGANIZER

CROSS-REFERENCE TO RELATED APPLICATIONS

This application claims priority to U.S. Provisional Patent Application No. 62/449,360, filed Jan. 23, 2017. The contents of which are incorporated herein by reference.

BACKGROUND

The present invention relates to organization devices for tubes, and more particularly to organization devices for retaining and organizing medical tubes on to a structure in a hospital such as a bedside rail, intravenous (IV) pole, wheelchair, and the like.

SUMMARY

Hospitalized patients may require multiple medical tubes for receiving different medications. The medical tubes may range in diameter and length, and may limit the amount of movement the patient can move. Specifically, the patient may be at least partially inhibited from movement within a hospital bed by the medical tubes. Further, transfer of the patient for testing or other needs that involve patient mobility, such as therapy, surgery, etc., may require movement of the medical tubes with the patient. The medical tubes may become disorganized and tangled during transfer of the patient. Furthermore, the medical tubes may be removed accidentally (e.g., dislodged) by tugging due to movement of the patient within the hospital bed, tripping or entanglement of a person (e.g., doctor, nurse, or visitor) on the medical tubes, or by catching on devices or persons during transport of the patient, and the like.

Embodiments described herein one or more of assist in organizing and retaining medical tubes, thereby reducing one or more of the aforementioned issues.

In one aspect, a medical tubing organizer includes a base defining a longitudinal direction, a lateral direction being defined as substantially orthogonal to the longitudinal direction, and a vertical direction being defined as substantially orthogonal to the longitudinal and lateral directions. A tube retainer is positioned on a top of the base and configured to receive a medical tube that extends along the lateral direction. The tube retainer is further configured to adjust between a free flow state and a retention state, wherein, in the free flow state, the tube retainer is configured to enable movement of the medical tube in the lateral direction and resist movement in the longitudinal direction, and in the retention state, the tube retainer is configured to resist movement in the lateral, longitudinal, and vertical directions. A connector is positioned on the base for selectively coupling the medical tubing organizer to a structure.

In another aspect, a method for organizing medical tubes including a base having a tube retainer and defining a longitudinal direction, the method including selectively coupling the base to a structure using a connector, receiving a medical tube in the tube retainer, and adjusting the tube retainer between a free flow state and a retention state. In the free flow state, the tube retainer allows movement of the medical tube in a lateral direction that is substantially orthogonal to the longitudinal direction, and resists movement of the medical tube in a vertical direction that is substantially orthogonal to the longitudinal and lateral directions. In the retention state, the tube retainer resists movement of the medical tube in the lateral and vertical directions.

In yet another aspect, a medical tubing organizer includes a base and a tube retainer positioned on a top of the base. The tube retainer includes a plurality of projections, each projection configured to receive a medical tube. A quantity of the plurality of projections is adjustable. A connector is positioned on the base for selectively coupling the medical tubing organizer to a structure.

Other aspects of the disclosure will become apparent by consideration of the detailed description and accompanying drawings.

BRIEF DESCRIPTION OF THE DRAWINGS

FIG. 9A is a perspective view of a medical tubing organizer according to a ninth embodiment, the medical tubing organizer in the free flow state.

FIG. 9B is another perspective view of the medical tubing organizer of FIG. 9A in the retention state.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Terms of degree, such as "substantially" or "approximately" are understood by those of ordinary skill to refer to reasonable ranges outside of the given value, for example, general tolerances associated with manufacturing, assembly, and use of the described embodiments. For example, "substantially" can be defined as being within about 5 percent to about 10 percent of a given value.

Illustrated herein are various embodiments of a medical tubing organizer for retaining and organizing medical tubes and selectively attached to a structure in a hospital or other medical setting, such as a bedside rail, IV pole, wheelchair, wall mount, and the like. Other medical settings may include a home of a patient after discharge, assisted living facility, nursing home, and the like.

Figure 1A:
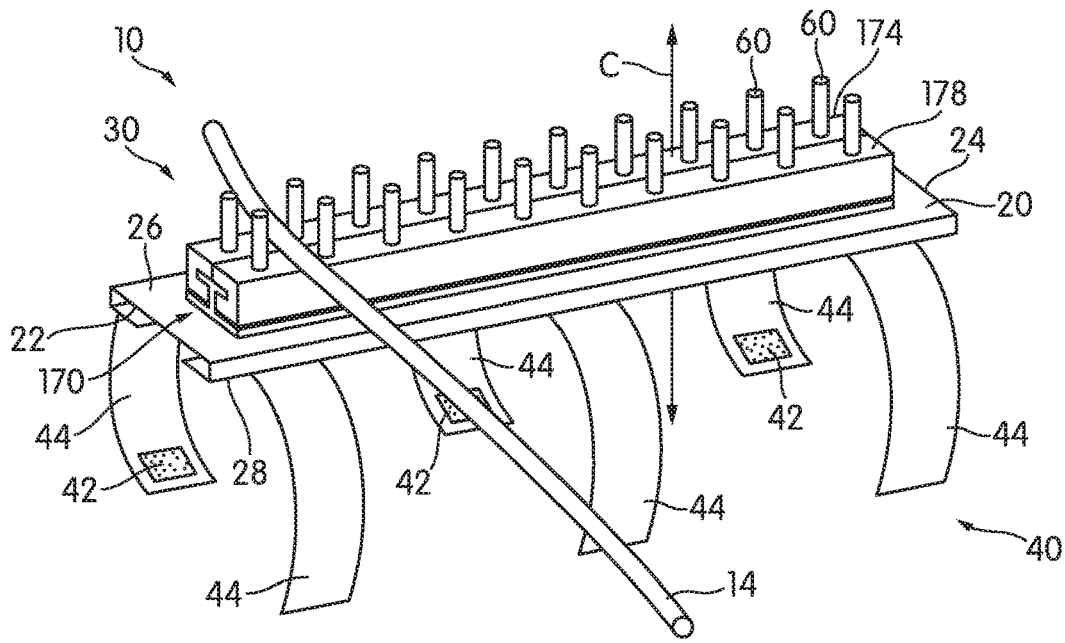
FIG. 1A is a perspective view of a medical tubing organizer according to one embodiment of the disclosure, the medical tubing organizer including a base, and straps and a tube retainer extending the base.
Figure 1B:
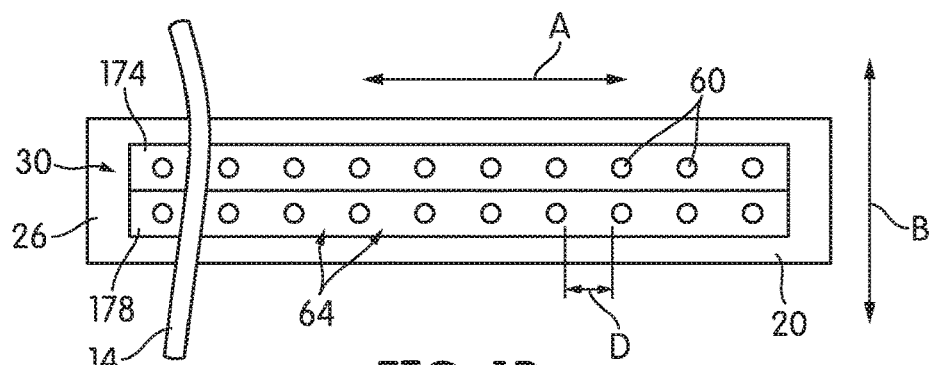
FIG. 1B is a top view of the medical tubing organizer of FIG. 1 in a free flow state.
Figure 1C:
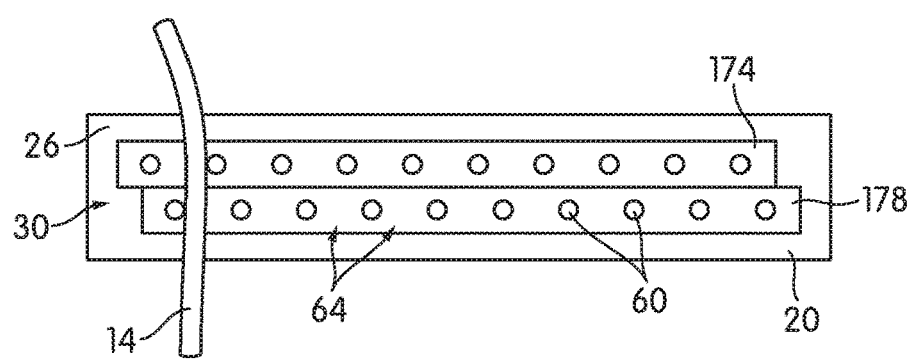
FIG. 1C is another top view of the medical tubing organizer of FIG. 1 in a retention state.

FIGS. 1A-C illustrate a medical tubing organizer 10 that retains and organizes one or more medical tubes 14. The medical tubing organizer 10 includes a base 20 and a tube retainer 30 positioned on the base 20. The tube retainer 30 is configured to receive at least one medical tube 14. The medical tubing organizer 10 further includes a connector 40 for selectively coupling the medical tubing organizer 10 to a structure 18, such as a bedside rail, IV pole, wall mount, wheelchair, patient arm, and the like (see FIG. 17).

The base 20 forms a three-dimensional shape including a first end 22 and a second end 24 opposite the first end 22. The illustrated base 20 is generally rectangular; however, in other constructions, the base 20 may have any desired shape, such as trapezoidal, square, pentagonal, and the like. For example, while the base 20 is rectangular in FIG. 1A, the base 20 is trapezoidal in other embodiments (see, e.g., the base 1620 shown in FIG. 16A). The base 20 includes a top or first side 26 extending from the first end 22 to the second end 24. A bottom or second side 28 is generally opposite the top 26. In some embodiments, as shown in FIG. 1A, the bottom 28 is substantially parallel to the top 26. The base 20 may be formed by a rigid material, such as plastic, wood, metal, and the like.

With reference to FIGS. 1A-1C, the base 20 defines a longitudinal direction A extending through the first end 22 and the second end 24. The top 26 of the base 20 extends along the longitudinal direction A. A lateral direction B is defined as being substantially orthogonal to the longitudinal direction A, and a vertical direction C is defined as being substantially orthogonal to the longitudinal and lateral directions A, B, respectively.

The tube retainer 30 is positioned on the top 26 of the base 20. The tube retainer 30 may be formed by a rigid material, a flexible material, or a combination of materials. For example, in FIG. 1A, the tube retainer 30 is formed by the rigid material, such as thermoplastics, cellulose, nylon, polystyrene, vinyl and acrylic or thermosets, epoxy or polyurethane formed by injection molding, extrusion molding or compression molding, or other as appropriate. The tube retainer 30 is configured to receive and retain the medical tube 14 extending along the lateral direction B (FIG. 1B). The tube retainer 30 may be configured to accommodate different sizes of the medical tube 14. For example, the size of the medical tube 14 may include a diameter between 0.125 Inches to 0.5 Inches. The tube retainer 30 may be further configured to accommodate the different sizes in the same medical tubing organizer 10, as further discussed below with respect to specific embodiments.

The tube retainer 30 is further configured to adjust between different states in which the tube retainer 30 may enable movement of the medical tube 14 in one of the longitudinal, lateral, vertical directions A, B, C and/or resist movement of the medical tube 14 in one of the longitudinal, lateral, vertical directions A, B, C within each state. Specifically, in a free flow state, the tube retainer 30 is configured to enable movement of the medical tube 14 in the lateral direction B and resist movement in the longitudinal direction A. In a retention state, the tube retainer 30 is configured to resist movement in the longitudinal, lateral, and vertical directions A, B, C.

More specifically, the tube retainer 30 includes a plurality of projections 60 movably coupled to the top 26 of the base 20. The tube retainer 30 further defines gaps 64 between adjacent projections 60. Each gap 64 is configured to receive the medical tube 14 and includes a size D defined between the adjacent projections 60. The projections 60 are configured to move relative to the base 20 for adjusting between the free flow state and the retention state.

To permit movement of the projections 60, the base 20 includes at least one track 170. The tube retainer 30 includes a first portion 174 and a second portion 178, one or both movably coupled to the tracks 170. Each portion 174, 178 includes at least some of the projections 60 extending away from the base 120 in the vertical direction C. The projections 60 are spaced apart substantially equally along the longitudinal direction A on the first and second portions 174, 178. Each gap 64 is defined between the aligned projections 60 of the first and second portions 174, 178. At least one of the first portion 174 and the second portion 178 is movable along the track 170 in the longitudinal direction A to adjust the tube retainer 30 between the free flow state and the retention state. Specifically, the projections 60 of the first portion 174 are aligned with the projections 60 of the second portion 178 in the free flow state (FIGS. 1A and 1B) and offset in the retention state (FIG. 1C). As such, the medical tube 14 may be sandwiched between the projections 60 in the gap 64 when the projections 60 of the first and second portions 174, 178 are offset such that the tube retainer 30 resists movement in the longitudinal, lateral, and vertical directions A, B, C (FIG. 1C). In the retention state, the friction provided by the offset protections 60 on the medical tube 14 resists the movement of the medical tube 14. The relative movement of the first and second portions 174, 178 decreases the size of the gaps 64 to cause the tube retainer 30 to enter the retention state, and increases the size of the gaps 64 to cause the tube retainer 30 to enter the free flow state. In some embodiments, in the retention state, the relative movement of the first and second portions 174, 178 offsets the projections 60 such that projections of the first portion 174 overlap the projections of the second portion 178 (i.e., the relative movement of the portions is even greater than that shown in FIG. 1C) and provide a winding path for the medical tube 14. The winding path increases the amount of resistive force provided by the projections 60 on the medical tube 14.

In some embodiments, the base 20 includes another track parallel and similar to the tracks 170 for movably coupling a third portion to the base 20 similar to the first and second portions 174, 178. For example, with reference to FIG. 1B, the third portion is provided below the second portion 178, such that the second portion 178 is between the first portion 174 and the third portion. The third portion includes projections 60 similar to the first and second portions 174, 178. In the free flow state, the projections 60 of the first portion 174, second portion 178, and third portion are aligned to provide the gap 64, similar to that which is shown in FIG. 1B. In the retention state, the second portion 178 moves relative to the first portion 174 and the third portion to offset the projections of the second portion 178 with respect to the projections 60 of the first portion 174 and the third portion. The offset of the projections 60, similar to those of FIG. 1C, render the gap 64 reduced in size and provide friction on the medical tube 14 to resist movement in the longitudinal, lateral, and vertical directions A, B, C.

The connector 40 is configured to hold the base 20 to the structure 18. More specifically, the connector 40 is configured to detachably couple to the structure 18 (see example structure 18 in FIG. 17). The connector 40 includes straps 44 extending from the base 20. The illustrated base 20 includes six straps 44 extending from the bottom 28 of the base 20; however, in other embodiments, more or fewer than six straps 44 extend from any side 26, 28 or end 22, 24 of the base 20. The illustrated straps 44 each include a hook and loop fastener 42 (e.g., Velcro™) for securing the straps 44 together around the structure 18. In other embodiments, in place of the fastener 42, a belt buckle connector is provided for each pair of straps 44. In other embodiments, the connector 40 may include a cable or zip tie mechanism including a first elongated portion having teeth and a second receptacle portion configured to receive the first elongated portion and engage the teeth of the first portion for connecting the medical tubing organizer 10 to the structure 18 (not shown). When the teeth are engaged with the second receptacle portion, the first and second portions form a loop whereby the teeth resist disengagement of the first and second portions. In still further embodiments, the connector 40 includes a hook and loop fastener 42 positioned on the bottom side 28 of the base 20 for securely mating with a hook and loop fastener positioned on the structure 18. In yet still further embodiments, the base 20 may include grooves formed on the bottom 28 of the base 20. The grooves may be configured to receive a track positioned on the structure 18 such as the bed rail, IV pole, etc. The grooves may also form a clamp for clamping onto the structure 18. Specifically, the grooves are formed by a flexible material such as foam, rubber, silicon, etc. that encompass the structure 18. As such, the base 20 is configured to be selectively attached to the structure 18 for ease of attachment/removal of the medical tubing organizer 10. Furthermore, the tube retainer 30 including the track 170 and the projections 60 may form a "sub-base" that can be removed from the base 20 such that the different tube retainers 30 described in the embodiments below may include any one or combination of the different connectors 40 described above.

Figure 17:
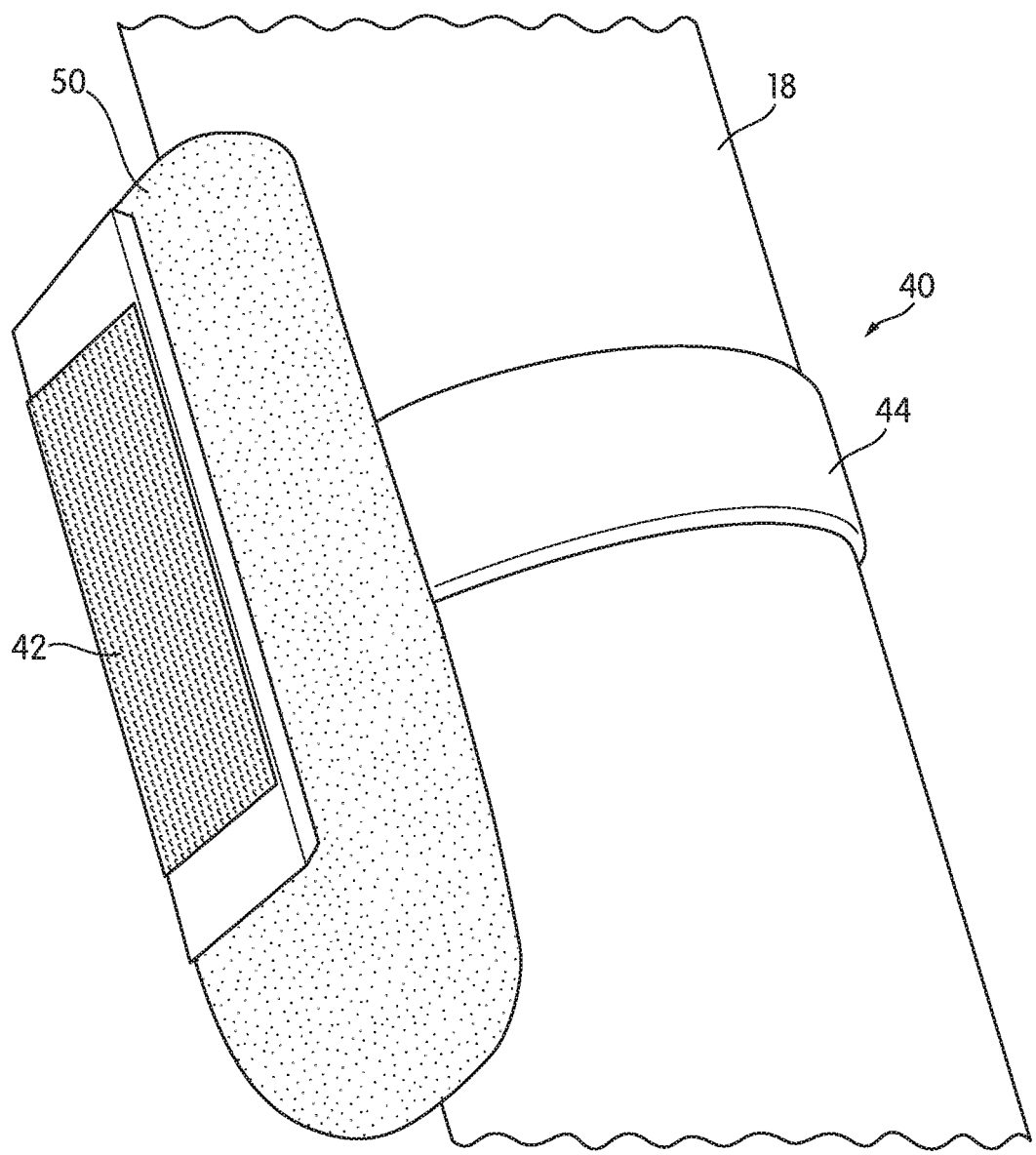
FIG. 17 is a perspective view of a pad having the straps of FIG. 1A and a hook and loop fastener for attaching the pad to the medical tubing organizer.

With reference to FIG. 17, the medical tubing organizer 10 may further include a pad 50 positioned between the base 20 and the structure 18. The pad 50 may be formed from flexible material such as foam, rubber, and the like. The illustrated pad 50 includes the connector 40 (e.g., strap 44) extending from the pad 50 for attaching the pad 50 to the structure 18, and fastener 42 for attaching the pad 50 to a hook and loop fastener on the bottom side 28 of the base 20. In other embodiments, the pad 50 may include other connectors 40 as described above. Furthermore, the pad 50 may be attached to the base 20 using an adhesive (not shown) such as epoxy or hot melt adhesive. The structure 18 may be a limb (e.g., arm) of a patient such that the medical tubing organizer 10 may be positioned on the patient.

FIGS. 2A-16C illustrate further embodiments of a medical tubing organizer for retaining and organizing medical tubes and selectively attached to the structure 18. The medical tubing organizers 210, 310, 410, 510, 610, 710, 810, 910, 1010, 1110, 1210, 1310, 1410, 1510, and 1610 of FIGS. 2A-16C are similar to the medical tubing organizer 10 illustrated in FIGS. 1A-C; therefore, similar components are designated with similar references numbers plus 100 for each new embodiment (i.e., plus 200 for the embodiment in FIGS. 2A-B, and 900 for the embodiment in FIGS. 9A-B), and only the differences between the medical tubing organizers will be discussed in detail. In addition, components or features described with respect to only one or some of the embodiments described herein are equally applicable to any other embodiments described herein. For example, the various connectors between bases and the structure 18 may be interchangeable between embodiments, as are the various adjustment mechanisms used for adjusting the projections used to retain the medical tubes, and as are the particular projection shapes used in the various embodiments.

Figure 2A:
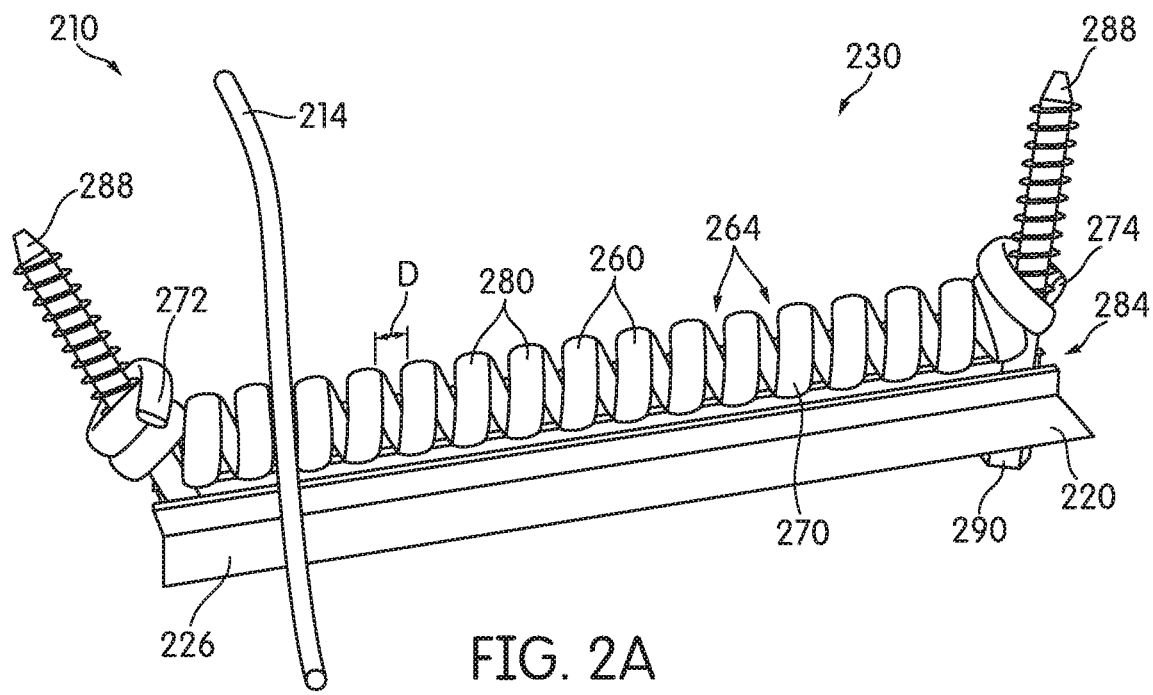
FIG. 2A is a perspective view of a medical tubing organizer according to a second embodiment, the medical tubing organizer in the free flow state.
Figure 2B:
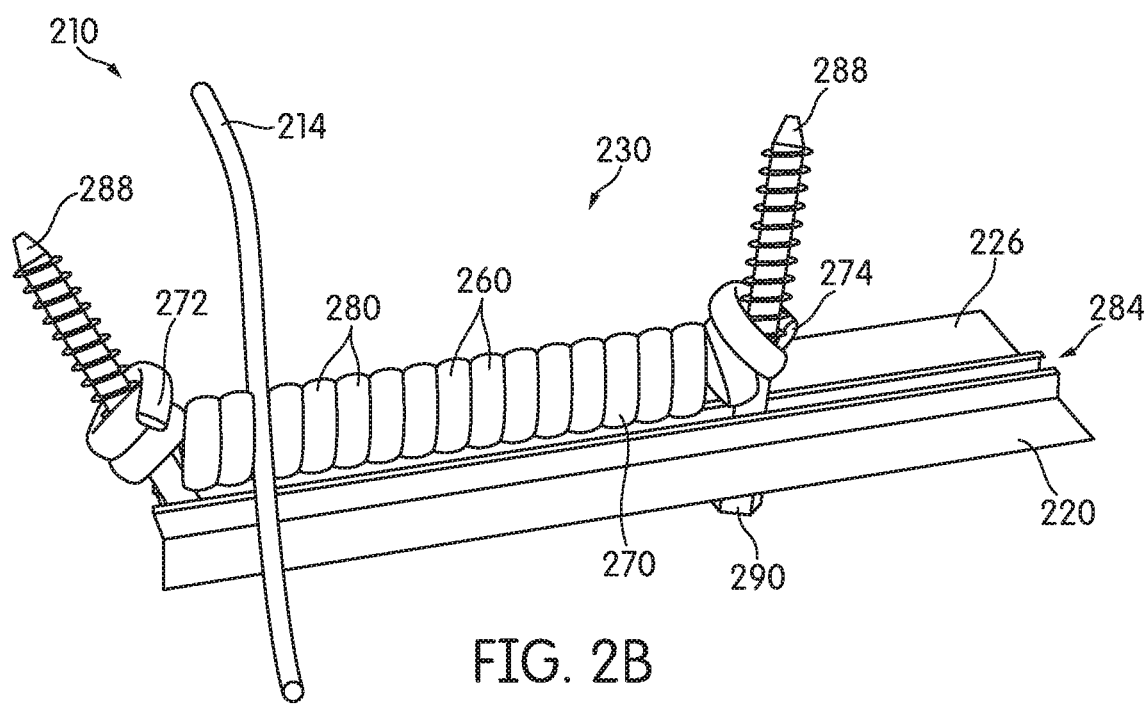
FIG. 2B is another perspective view of the medical tubing organizer of FIG. 2A in the retention state.
Figure 3A:
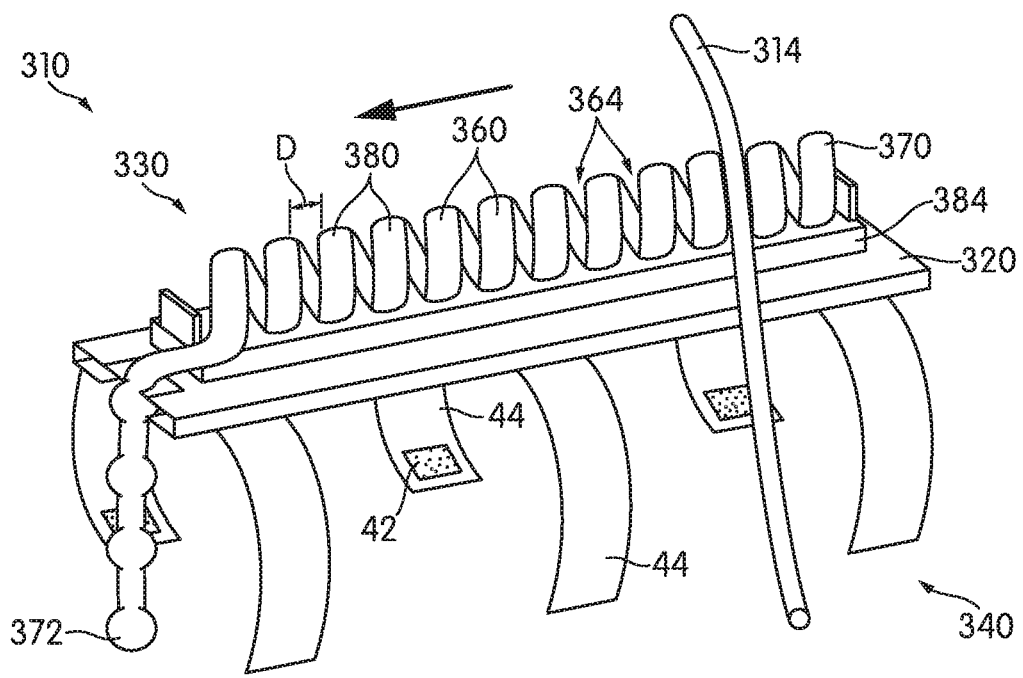
FIG. 3A is a perspective view of a medical tubing organizer according to a third embodiment, the medical tubing organizer in the free flow state.
Figure 3B:
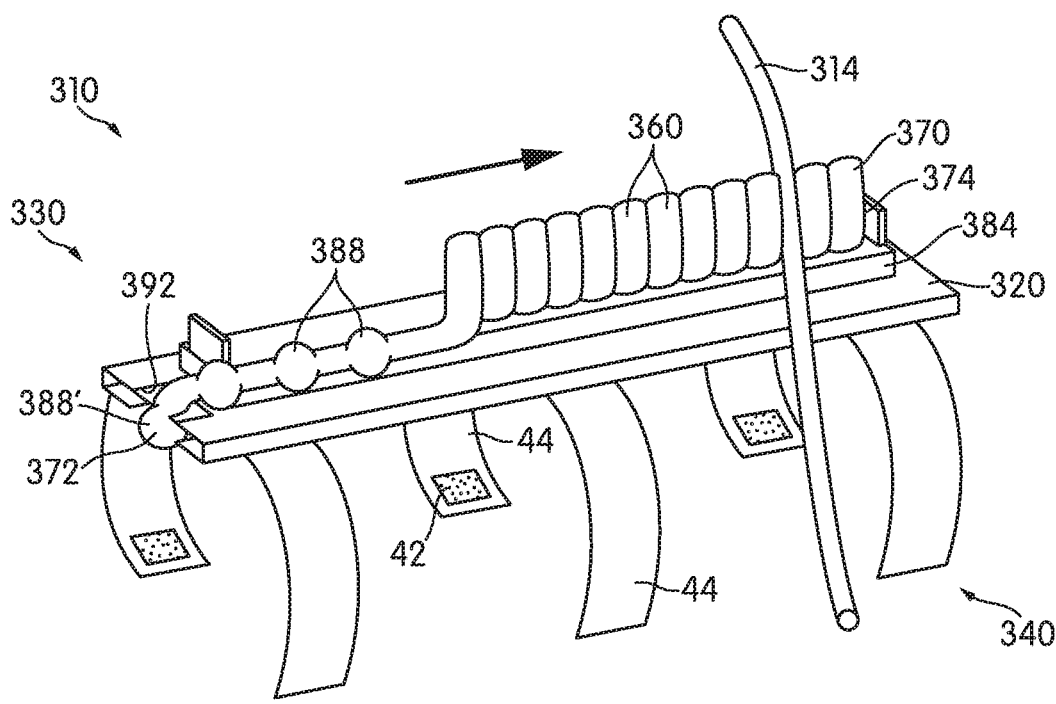
FIG. 3B is another perspective view of the medical tubing organizer of FIG. 3A in the retention state.

With reference to the medical tubing organizers 210, 310 of FIGS. 2 and 3, the tube retainer 230, 330 includes a coil spring member 270, 370 positioned on the top 226, 326 of the base 220, 320 and having a first end 272, 372 and a second end 274, 374. The coil spring member 230, 330 includes continuous loops or coils 280, 380 to form the plurality of projections 260, 360 which extend from the first end 272, 372 to the second end 274, 374. Each of the gaps 264, 364 is defined between adjacent coils 280, 380. Furthermore, at least one of the first end 272, 372 and the second end 274, 374 of the coil spring member 270, 370 is movably coupled to a track 284, 384 of the base 220, 320 such that the size D of the gaps 264, 364 between the adjacent projections 260, 360 (i.e., coils 280) is altered. As such, movement of the first end 272, 372 and/or the second end 274, 374 alters (i.e., increases or decreases) the gaps 264, 364 between the coils 280, 380 for adjusting the tube retainer 230, 330 between the free flow state (FIGS. 2A and 3A) and the retention state (FIGS. 2B and 3B). As shown in FIGS. 2A-2B, the second end 274 is movable relative to the track 284. Conversely, as shown in FIGS. 3A-3B, the first end 372 is movable relative to the track 384. In the free flow state, the tube retainer 230, 330 is configured to enable movement of the medical tube 14 in the lateral direction B and resist movement in the longitudinal direction A. In a retention state, the tube retainer 230, 330 is configured to resist movement in the longitudinal, lateral, and vertical directions A, B, C.

With reference to FIG. 2, the tube retainer 230 includes arms 288 (e.g., a bolt including a threaded portion and a head portion) positioned at each end 272, 274 of the coil spring member 270. At least one or both of the arms 288 is movably coupled to the track 284 for altering the size D of the gaps 264. Furthermore, the illustrated tube retainer 230 includes a locking member 290, such as a wing nut, positioned on the movable arm 288. The locking member 290 is threaded and rotatable about threads of the arm 288 for securing the arm 288 in a particular longitudinal position along the track 284, thereby securing the tube retainer 230 in the free flow state and the retention state. In other words, with the arm 288 in the position illustrated in FIG. 2A and the locking member 290 tightened, the tube retainer 230 is secured in the free flow state. With the arm 288 in the position illustrated in FIG. 2B and the locking member 290 tightened, the tube retainer 230 is secured in the retention state. The arms 288 or at least ends of the arms 288 may include a flexible material such as rubber, silicon, etc. to provide protection to the patient. Specifically, the arms 288 may include the flexible material such that the arms 288 may not include a hard or pointed edge for providing the protection. In some embodiments, other locking members 290 are provided to maintain the ends of the coil 270 in a desired position, such as a buckle that arm 288 clips into at an end of the base 230 or a mechanism such as shown and described with respect to FIGS. 6A-B below.

With reference to FIG. 3, the coil spring member 370 includes protrusions 388. The illustrated protrusions 388 have a spherical shape and are spaced along at least a portion of the coil spring member 370, such as along a first end of the coil spring member 370. In other embodiments, the protrusions 388 have another shape, such as rectangular, square, or the like. The base 320 further includes an opening 392 positioned at one of the ends 322, 324 of the base 320. The opening 392 is configured to receive the coil spring member 370, but sized to prevent passage of the protrusions 388, such that the protrusions 388 hold the tube retainer 330 in the free flow state (FIG. 3A) and the retention state (FIG. 3B). For example, when the opening 392 receives the coil spring member 370 adjacent one of the protrusions 388' that is near the first end 372 of the coil spring member 370, the tube retainer 330 is in the retention state (FIG. 3B). However, when the opening 392 receives the coil spring member 370 adjacent one of the protrusions 388 that is nearer to second end 374, the tube retainer 330 is in the free flow state (FIG. 3A).

Figure 4A:
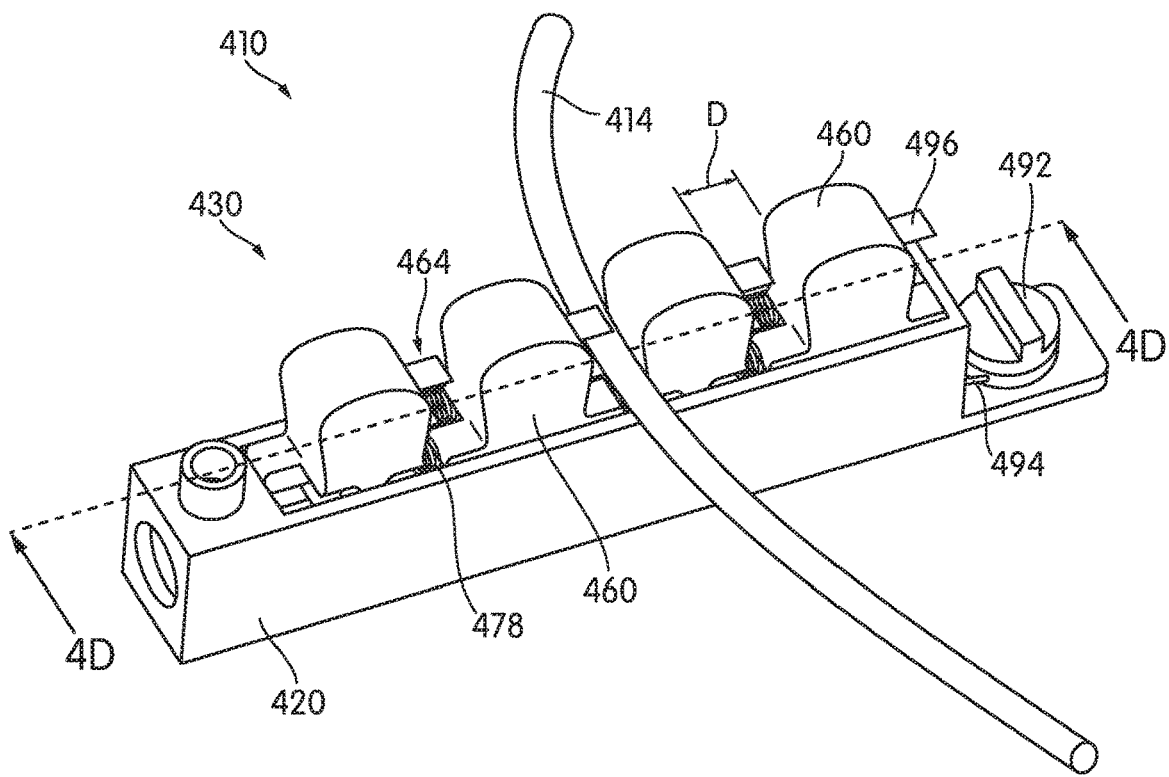
FIG. 4A is a perspective view of a medical tubing organizer according to a fourth embodiment, the medical tubing organizer in an open state.
Figure 4B:
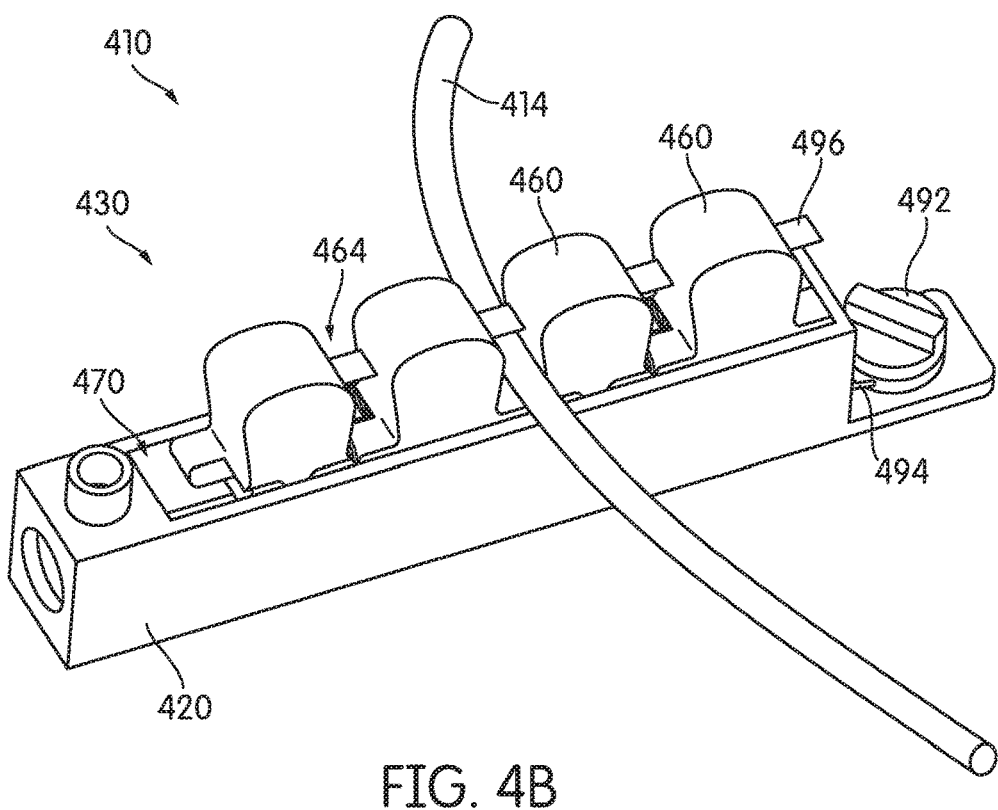
FIG. 4B is another perspective view of the medical tubing organizer of FIG. 4A in the free flow state.
Figure 4C:
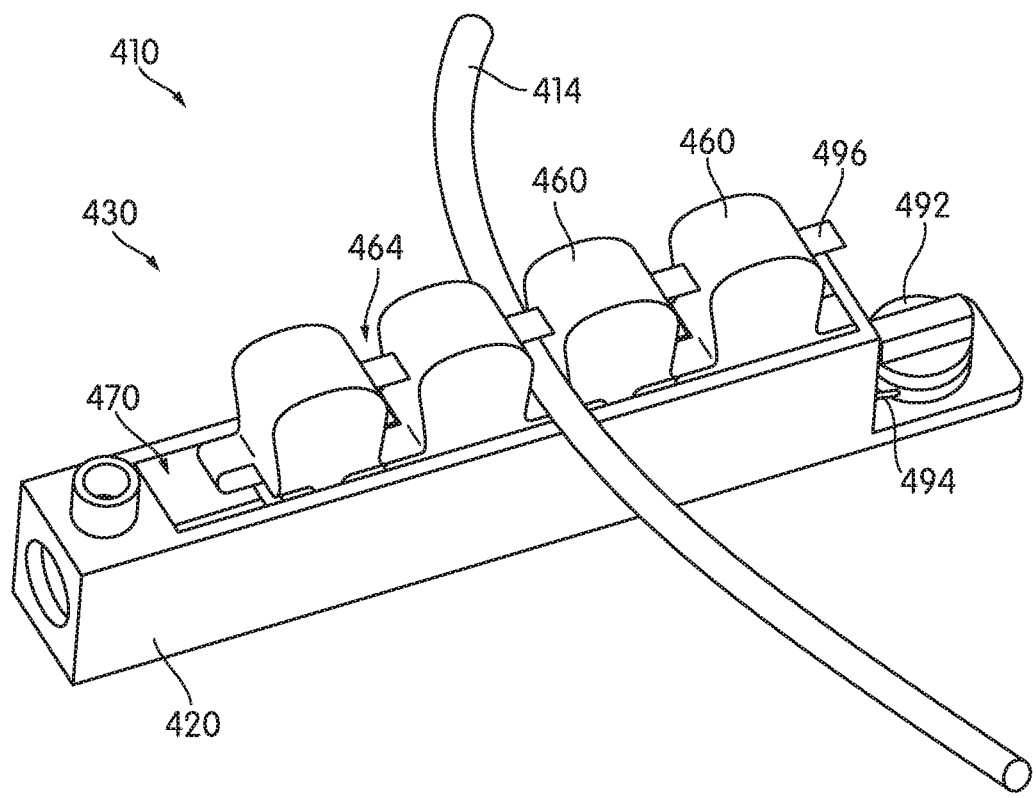
FIG. 4C is still another perspective view of the medical tubing organizer of FIG. 4A in the retention state.
Figure 4D:
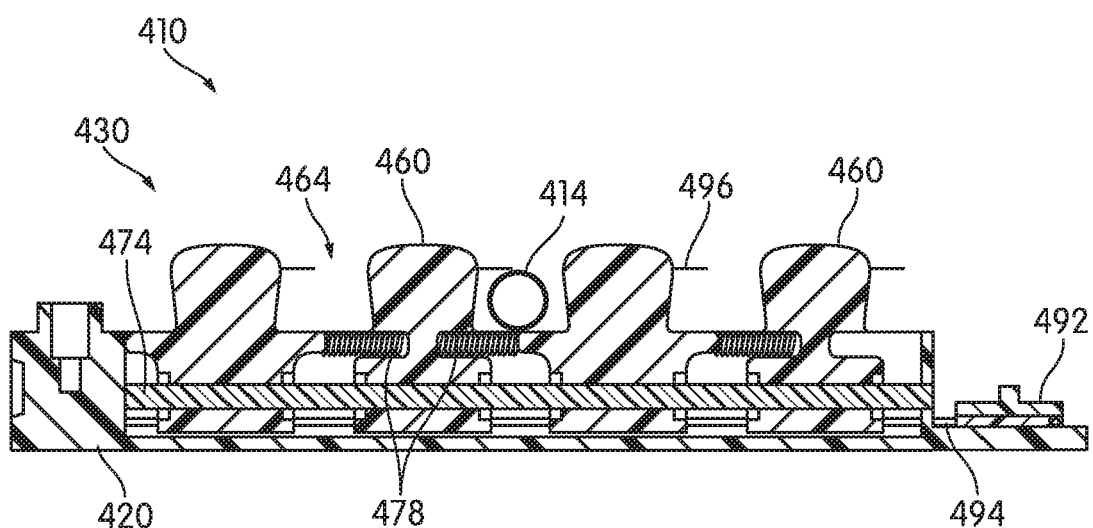
FIG. 4D is a cross sectional view of the medical tubing organizer viewed along section 4D-4D of FIG. 4A.

With reference to FIGS. 4A-4D, the base 420 defines a chamber 470 having a linear rail 474 (FIG. 4D) supported within the chamber 470. The illustrated projections 460 are generally cylindrical in shape and are slidably coupled to the rail 474. A number of the projections 460 is adjustable. For example, in the illustrated embodiment, the number of projections 460 is four; however, in other embodiment, the number of projections 460 is more or fewer than four. Each projection 460 extends from the rail 474 in the vertical direction C. Additionally, each coil of a spring 478 (FIG. 4D) is positioned between the adjacent projections 460 to separate each projection 460. The base 420 includes a rotatable knob 492 and pulley 494 that is connected to the spring 478 and projections 460. The rotation of the knob 492 alters (i.e., increases or decreases) the gaps 464 between the projections 460 for adjusting the tube retainer 430 between an open state (FIG. 4A), the free flow state (FIG. 4B) and the retention state (FIG. 4C). More specifically, the rotation of the knob 492 in one direction moves the projections 460 closer together using the spring 478 and the pulley 494 along the longitudinal direction A, and the rotation of the knob 492 in the other direction moves the projections 460 farther apart using the spring 478 and the pulley 494 along the longitudinal direction A. Moreover, the combination of the knob 492, pulley 494, and spring 478 is configured to provide the substantially the same amount of retention to each medical tube 414 within each gap 464 regardless of the size of the medical tube 414. As such, the tube retainer 430 is configured to retain medical tubes 414 of different sizes within the gaps 464 in each of the open state, the free flow state, and the retention state.

In the open state, the tube retainer 430 is configured to enable movement of the medical tube 414 in the lateral direction B and provide some resistance or limits on movement in the longitudinal direction A. In the free flow state, the tube retainer 430 is configured to enable movement of the medical tube 414 in the lateral direction B and to resist or limit movement in the longitudinal direction A more than in the open state. In a retention state, the tube retainer 430 is configured to resist movement in the longitudinal, lateral, and vertical directions A, B, C.

With continued reference to FIGS. 4A-4D, each projection 460 may further include a flange 496 extending from a side of at least one of the projections 460 along the longitudinal direction A. The flange 496 is configured to resist movement of the medical tube 414 in the vertical direction C when the tube retainer 430 is in the retention state and in the free flow state. In other embodiments, the flange 496 is not included.

The projections 460 may be formed by a rigid material, a flexible material, or a combination of materials. For example, as illustrated, the projections 460 are formed by a rigid material, such as thermoplastics or thermosets. However, in some embodiments, the projections 460 are formed by a flexible material, such as foam.

Figure 5A:
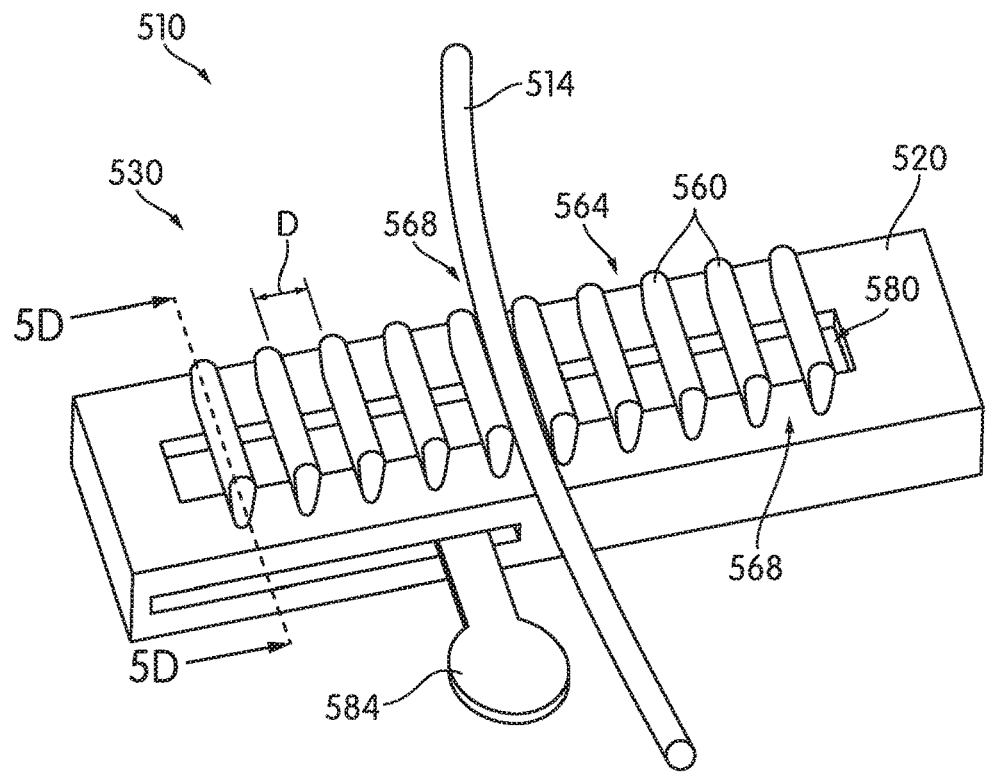
FIG. 5A is a perspective view of a medical tubing organizer according to a fifth embodiment, the medical tubing organizer in the open state.
Figure 5B:
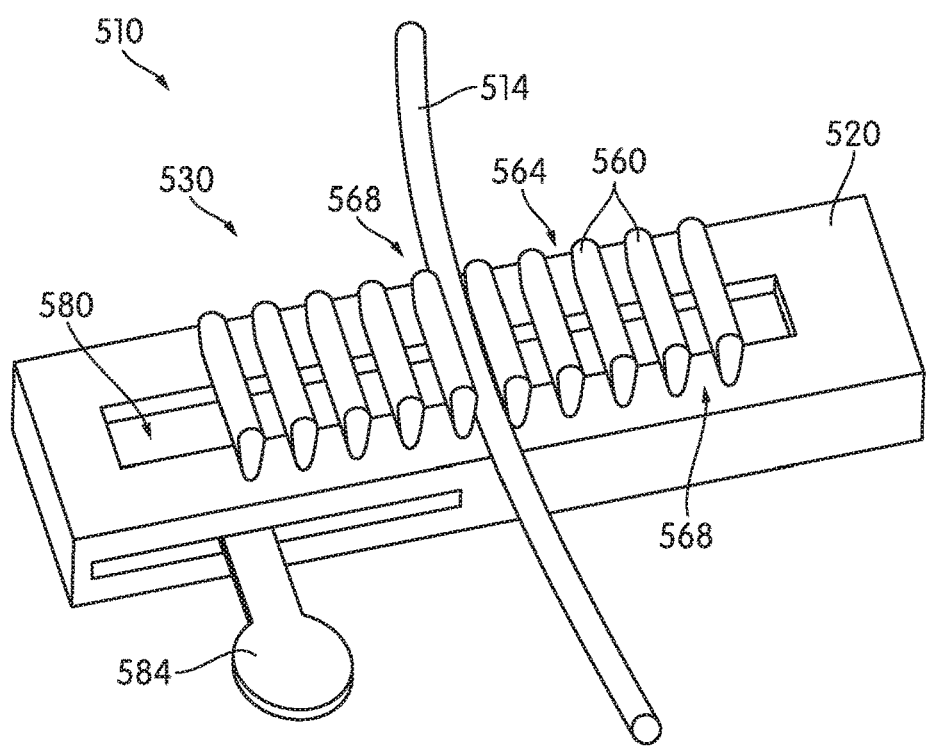
FIG. 5B is another perspective view of the medical tubing organizer of FIG. 5A in the free flow state.
Figure 5C:
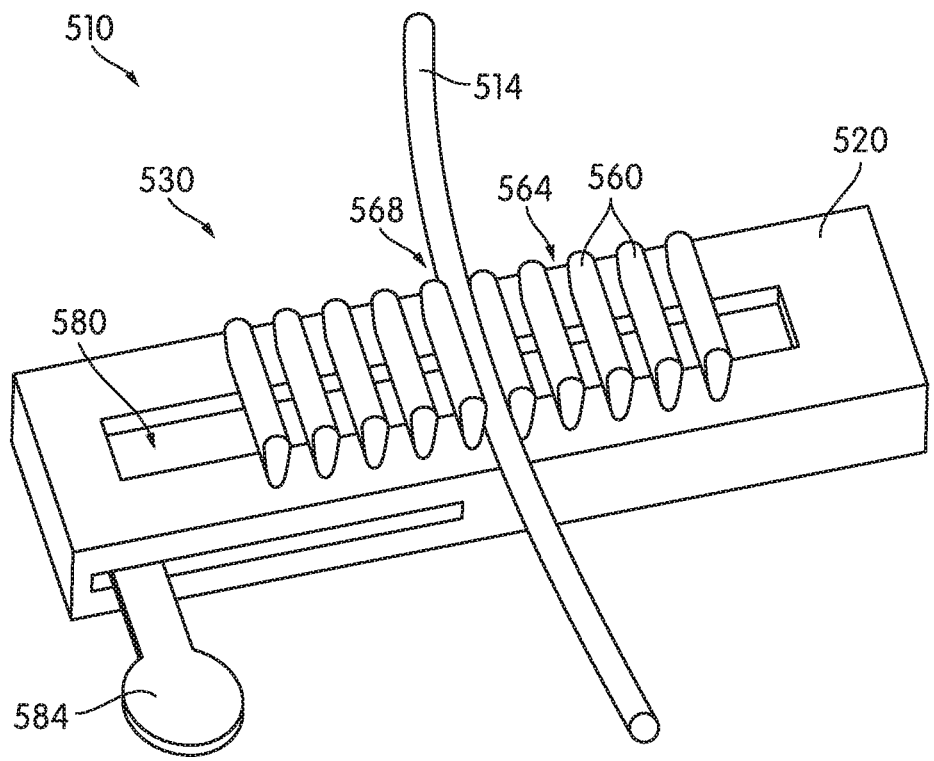
FIG. 5C is still another perspective view of the medical tubing organizer of FIG. 5A in the retention state.
Figure 5D:
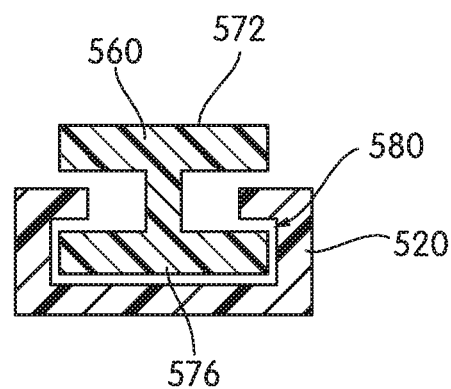
FIG. 5D is a cross sectional view of the medical tubing organizer viewed along section 5D-5D of FIG. 5A.

With reference to FIGS. 5A-5D, the plurality of projections 560 includes pairs of projections 568 formed by the adjacent projections 560. As shown in FIG. 5A, the tube retainer 530 includes five pairs of projections 568; however, in other embodiments, the number of pairs 568 may be more or fewer than five. Each of the pair of projections 568 defines the gap 564 configured to receive the medical tube 514. The projections have an I-shape cross section (FIG. 5D) including a top flange 572 and a bottom flange 576. Moreover, the base 520 defines a cavity 580 configured to receive the bottom flange 576 of each projection 560. Coils of a spring (not shown) are positioned between the pairs or projections 568 for altering the size D of each gap 564, similar to the spring 478 fourth embodiment (FIGS. 4A-4D). More specifically, one or both of the projections 560 of each of the pairs of projections 568 moves relative to each other along the longitudinal axis A using a lever 584 connected to the spring for adjusting the tube retainer 530 between the open state (FIG. 5A), the free flow state (FIG. 5B), and the retention state (FIG. 5C). For example, as shown in FIGS. 5A-5C, the lever 584 is adjusted such that the spring forces each projection 560 of the pair of projections 568 towards each other along the longitudinal axis A and/or towards one end of the tube retainer 530.

In the open state, the tube retainer 530 is configured to enable movement of the medical tube 514 in the lateral direction B and provide some resistance or limits on movement in the longitudinal direction A. In the free flow state, the tube retainer 530 is configured to enable movement of the medical tube 514 in the lateral direction B and to resist or limit movement in the longitudinal direction A more than in the open state. In a retention state, the tube retainer 530 is configured to resist movement in the longitudinal, lateral, and vertical directions A, B, C. In some embodiments, friction between the protrusions 560 and the medical tube 514 may reduce ease of movement along the lateral direction B such that the movement of the medical tube 514 is further restricted. As such, a level of the resistance in the free flow state and/or the retention state may vary (i.e., more or less resistance) such that the movement of the medical tube 514 may be further restricted in both the free flow state and the retention state.

Figure 6A:
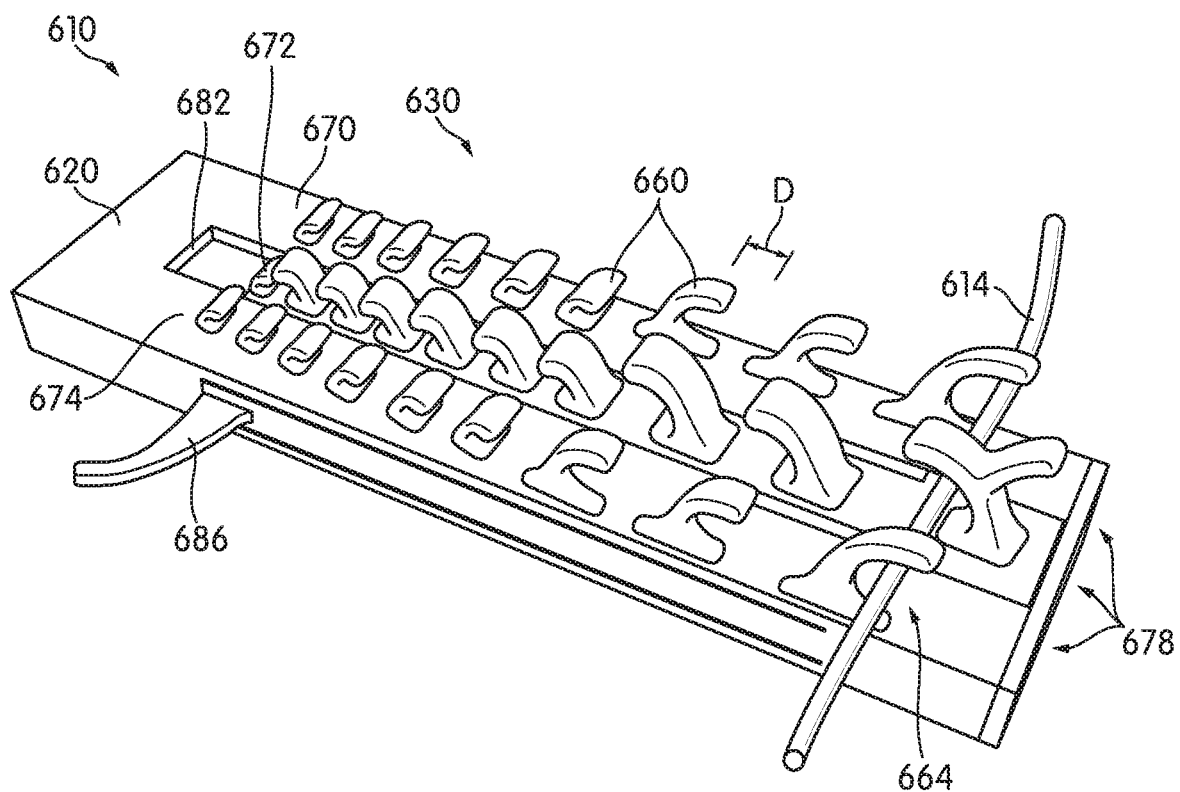
FIG. 6A is a perspective view of a medical tubing organizer according to a sixth embodiment, the medical tubing organizer in the free flow state.
Figure 6B:
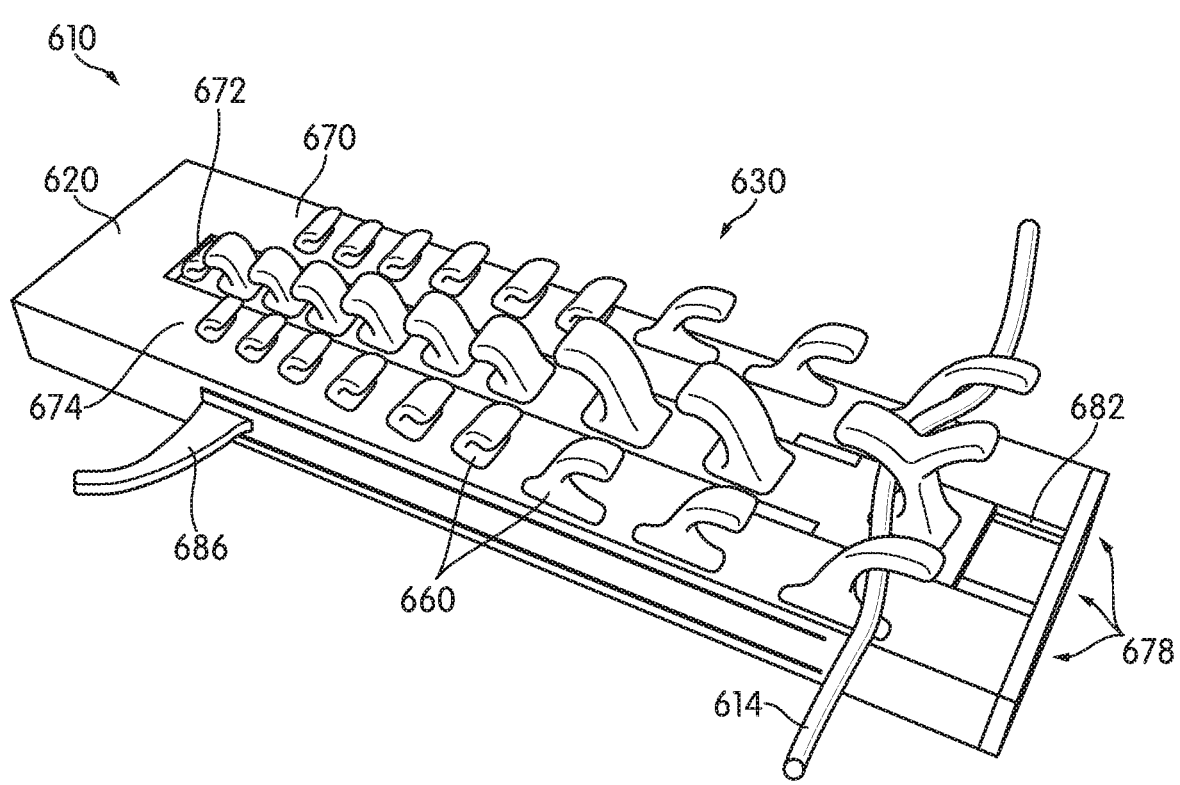
FIG. 6B is another perspective view of the medical tubing organizer of FIG. 6A in the retention state.

With reference to FIGS. 6A-6B, the tube retainer 630 includes first, second and third portions 670, 672, 674, each including a row of projections 678. The projections 660 are spaced apart along the longitudinal direction A on the three portions 670, 672, 674. Each gap 664 is defined between the aligned projections 660 of the three portions 670, 672, 674. Furthermore, the side D of each gap 664 may decrease along the longitudinal direction A on each portion 670, 672, 674 such that the tube retainer 630 is configured to retain medical tubes 614 of different sizes. The second, middle portion 672 is movable along a track 682 in the longitudinal direction A to adjust the tube retainer 630 between the free flow state and the retention state. Specifically, the projections 660 of the three portions 670, 672, 674 are aligned in the free flow state (FIG. 6A) and offset in the retention state (FIG. 6B). As such, the medical tube 614 may be sandwiched between the projections 660 in the gap 664 when the projections 660 are offset such that the tube retainer 630 resists movement in the longitudinal, lateral, and vertical directions A, B, C (FIG. 6B).

With continued reference to FIGS. 6A-6B, a spring and ratchet (not shown) is positioned within the base 620. The spring and ratchet is used to adjust a position of the second portion 672 relative to the other two portions 670, 674. Specifically, a force may be applied manually to the second portion 672 for moving the second portion 672 relative to the other portions 670, 674. Furthermore, a lever 686 is connected to the spring and ratchet. The spring and ratchet maintain the longitudinal position of the second portion 672 with respect to the first and third portions 670, 674. When the lever is pulled away from the base 670 along the lateral direction B, the spring and ratchet are released such that the tube retainer 630 is adjustable into the open state from the retention state.

In the free flow state, the tube retainer 630 is configured to enable movement of the medical tube 614 in the lateral direction B and to resist movement in the longitudinal direction A. Additionally, because of the curve of the projections 660, the tube retainer 630 resists movement of the medical tube in the vertical direction C when in the free flow state. In a retention state, the tube retainer 630 is configured to resist movement in the longitudinal, lateral, and vertical directions A, B, C.

Figure 7A:
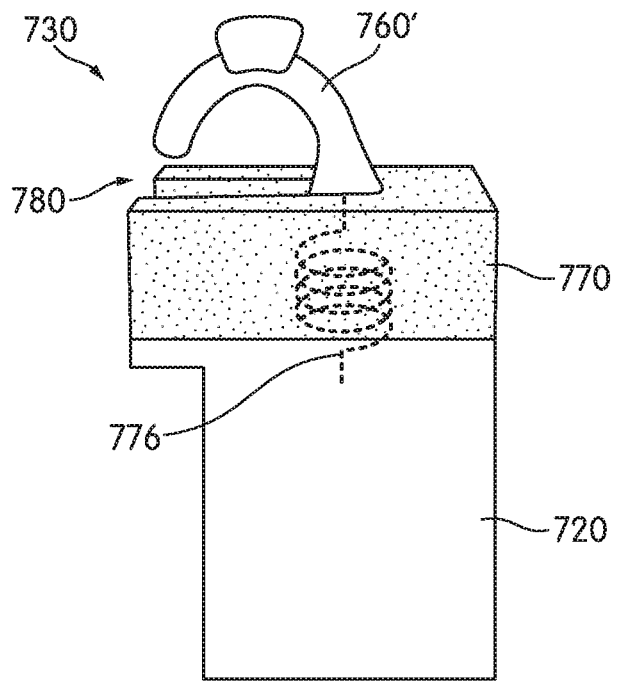
FIG. 7A is a perspective view of a medical tubing organizer according to a seventh embodiment, the medical tubing organizer in the open state.
Figure 7B:
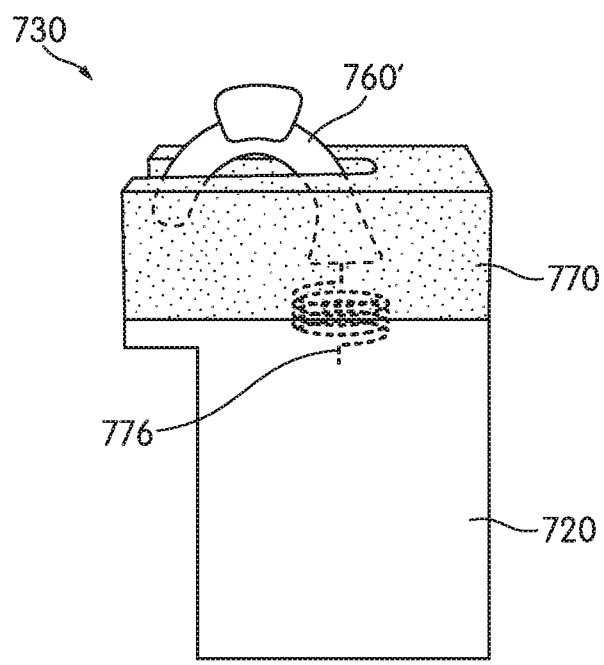
FIG. 7B is another perspective view of the medical tubing organizer of FIG. 7A in the retention state.

FIGS. 7A-7B illustrates a tube retainer 730 including one projection 760' of a plurality of projections 760 that may be attached together in one row. For example, in one embodiment, the projections 760 are configured to be selectively attached to a track of a base similar to the embodiment of FIGS. 13A-B discussed in further detail below. Alternatively, the projections 760 may be attached to a base (similar to the base 20) using a hook and loop fastener (not shown). As such, the number of projections 760 is adjustable. The tube retainer 730 includes the at least one projection 760' extending from a head 770. The head 770 is coupled to the base 720. As such, in some embodiments, the base 720 is formed by multiple portions attached together. Furthermore, each projection 760 is attached to a spring 776 positioned within at least the head 770. The spring 776 is configured to bias the projection 760' downwardly towards the base 720 along the vertical axis C. As shown in FIG. 7A, the projection 760' may be pulled upwardly along the vertical direction C to provide an entry point 780 at a free end of the projection 760' for the medical tube (not shown) between the projection 760' and the base 720. Therefore, the tube retainer 730 is adjustable between the open state (FIG. 7A) and the retention state (FIG. 7B). Moreover, the entry point 780 is operable to accommodate the medical tubes 714 of different sizes by selective movement of the spring along the vertical direction C (i.e., upwards against the bias of the spring 776, downwards using the spring 776) such that the tube retainer 730 is configured to retain the medical tubes 714 of different sizes in each of the open state and the retention state.

In the free flow state, the tube retainer 730 is configured to enable movement of the medical tube 14 in the lateral direction B and to resist movement in the longitudinal direction A. Additionally, because of the curve of the projections 760', the tube retainer 730 resists movement of the medical tube 14 in the vertical direction C when in the free flow state. In a retention state, the tube retainer 730 is configured to resist movement in the longitudinal, lateral, and vertical directions A, B, C.

Figure 8A:
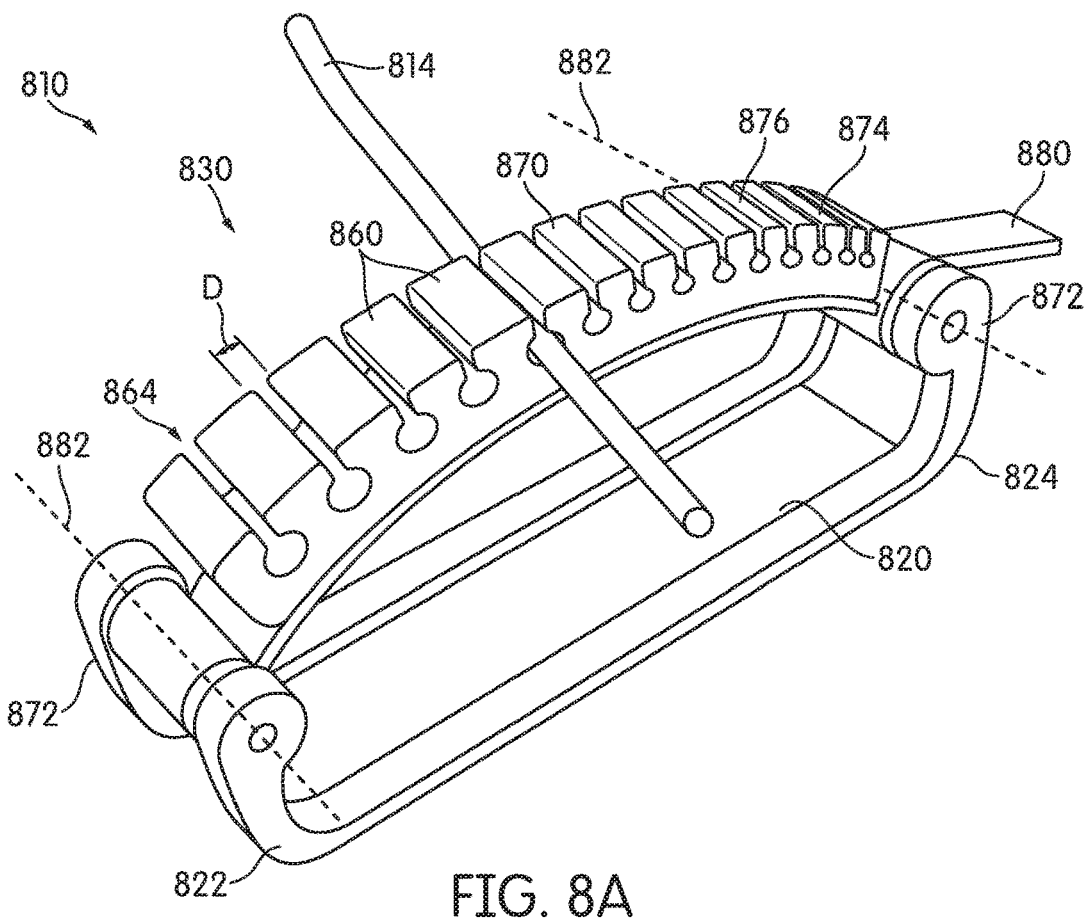
FIG. 8A is a perspective view of a medical tubing organizer according to an eighth embodiment, the medical tubing organizer in the free flow state.
Figure 8B:
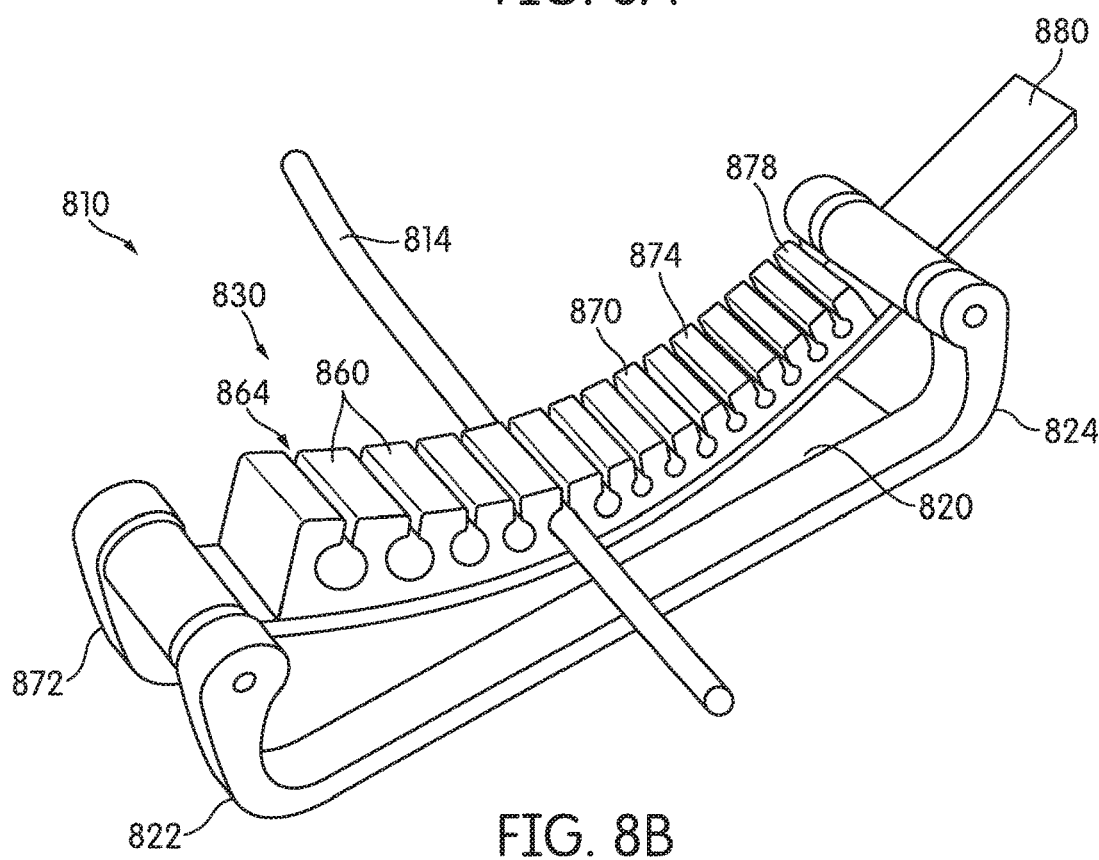
FIG. 8B is another perspective view of the medical tubing organizer of FIG. 8A in the retention state.

With reference to FIGS. 8A-8B, the tube retainer 830 includes a bendable body 870 positioned between sides 872 extending from each end 822, 824 of the base 820 in the vertical direction C. A top side 874 of the body 870 defines the plurality of projections 860. The projections 860 are separated by the gaps 864. The body 870 is rotatably coupled to the sides 872 for rotating the body 870 between a convex shape 876 and a concave shape 878. The body 870 further includes a handle 880 rotatable about one of the sides 872. Specifically, the handle 880 rotates about one of the axes 882 defined by each side 872. As such, rotating the handle 880 clockwise rotates the body 870 about the sides 872 into the convex shape 876, and rotating the handle 880 counterclockwise rotates the body 870 about the sides 872 into the concave shape 878. The body 870 is formed by the flexible material, such as foam, rubber, or silicon, for adjusting between the two shapes 876, 878.

Furthermore, the size D of the gaps 864 between the projections 860 is altered by switching between the two shapes 876, 878 for adjusting between the free flow state and the retention state. Specifically, when the body 870 is in a first, convex position, the size D of the gap 864 increases such that the body 870 in the free flow state. In the free flow state, the tube retainer 830 is configured to enable movement of the medical tube 814 in the lateral direction B and to resist movement in the longitudinal direction A. Additionally, because of the gaps 864 between the projections 860 have a narrow top channel portion leading to a wider bottom portion, the tube retainer 830 resists movement of the medical tube 814 in the vertical direction C when in the free flow state. When the body 870 is in a second, concave position, the size D of the gap 864 decreases such that the body 870 is in the retention state. In the retention state, the tube retainer 830 is configured to resist movement in the longitudinal, lateral, and vertical directions A, B, C. More particularly, the projections 860 on both sides of the medical tube 814 engage the medical tube 814 to resist movement thereof.

With reference to FIGS. 9A-9B, the tube retainer 930 includes a bendable body 970 and an elongated member 974 extending from a side of the body 970. A top side 978 of the body 970 defines the plurality of projections 960, which extend away from a base 920. In some embodiments, a connector, similar to the connector 42 of FIG. 14B (described below) is provided on the bottom side of the base 920 to enable the tube retainer 930 to be attached to the structure 18.

The projections 960 are separated by the gaps 964. The illustrated gaps 964 include different sizes for accommodating medical tubes (not shown) of different sizes. The base 920 is flexible, and the elongated member 974 is configured to enclose (i.e., wrap) around the body 970 for adjusting the tube retainer 930 between the free flow state (FIG. 9A) and the retention state (FIG. 9B). Specifically, the elongated member 974 wraps over a top 982 the projections 960 and attaches to the body 970 such that the gaps 964 between the projections 960 are altered (i.e., decreased). The elongated member 974 may be attached to the body 970 using a hook and loop fastener 986, such as Velcro™.

In the free flow state, the tube retainer 930 is configured to enable movement of the medical tube 14 in the lateral direction B and to resist movement in the longitudinal direction A. Additionally, because of the gaps 964 between the projections 960 have a narrow top channel portion leading to a wider bottom portion, the tube retainer 930 resists movement of the medical tube 14 in the vertical direction C when in the free flow state. When in the retention state, the tube retainer 930 is configured to resist movement in the longitudinal, lateral, and vertical directions A, B, C. More particularly, the projections 960 on both sides of the medical tube 14 engage the medical tube 14 to resist movement thereof.

Figure 10A:
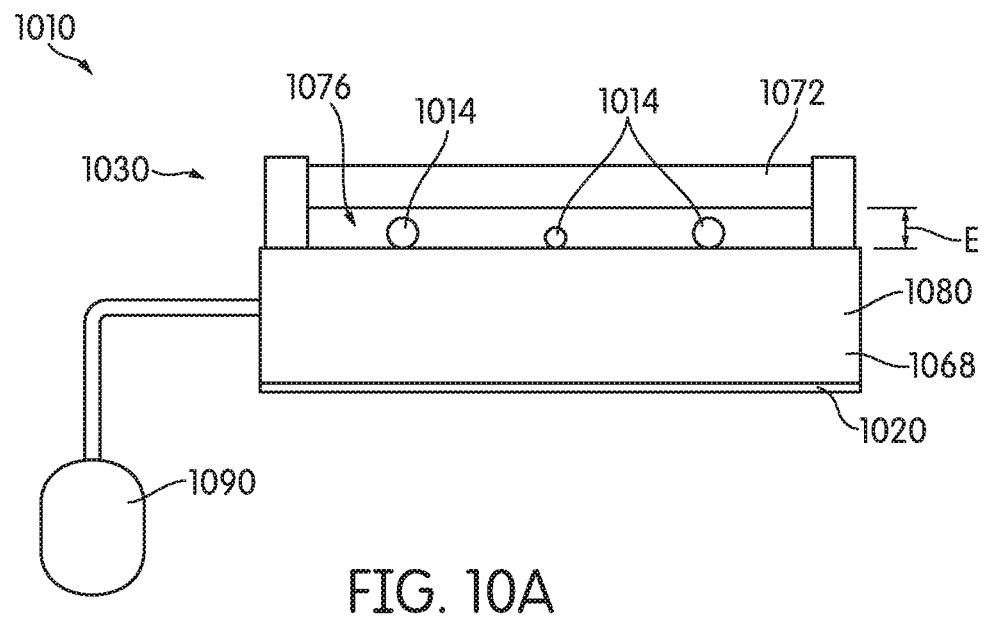
FIG. 10A is a schematic view of a medical tubing organizer according to a tenth embodiment, the medical tubing organizer in the free flow state.
Figure 10B:
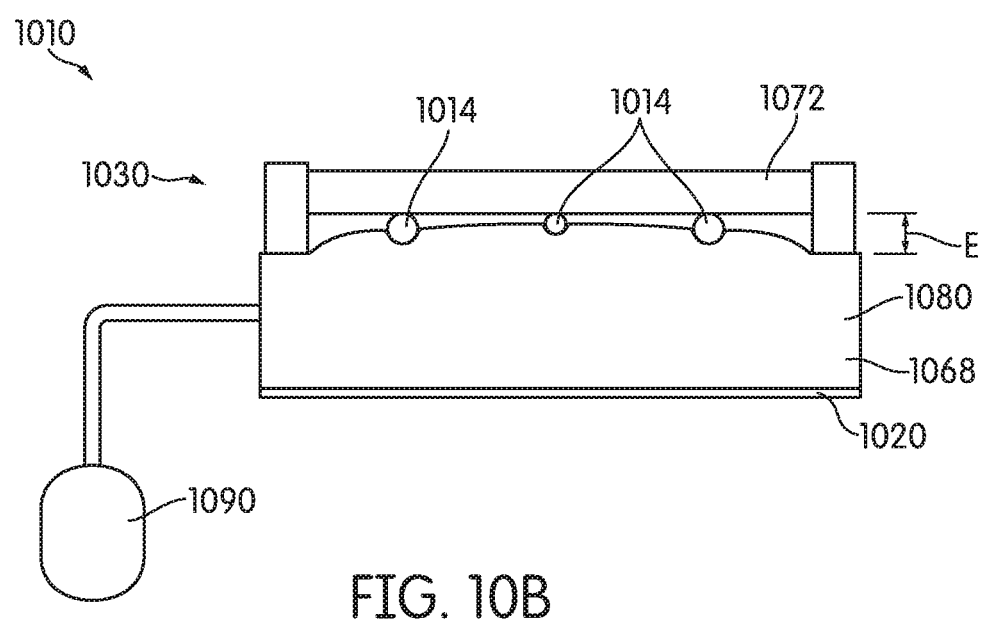
FIG. 10B is another schematic view of the medical tubing organizer of FIG. 10A in the retention state.

FIGS. 10A-10B illustrate a schematic view of the tube retainer 1030. The tube retainer 1030 includes a first body portion 1068 coupled to the top 1026 of the base 1020 and a second body portion 1072 positioned above the first body portion 1068. In some embodiments, the second body portion 1072 attaches to the first body portion 1068 via a hinge (not shown) at one end (e.g., the right side, in FIG. 10A) and a latch (not shown) at the other end, such that the second body portion 1072 opens to enable placement of the medical tubes 1014 into tube retainer 1030 (i.e., an open state) and securely closes, such as shown in FIGS. 10A-B. The hinge and latch may be similar to that which is shown in and described with respect to FIG. 11.

The first and second body portions 1068, 1072 define a gap 1076 configured to receive the at least one medical tube 1014. The gap 1076 includes a size E that may be altered (increased or decreased) using pneumatics for adjusting the tube retainer 1030 between the free flow state and the retention state. Specifically, the first body portion 1068 defines a chamber 1080 configured to receive a gas, such as air, provided by manual manipulation (e.g., squeezing by hand) a pump 1090 in fluid communication with the chamber 1080. A release valve (not shown) is also provided (e.g., adjacent the pump 1090) to allow the gas to exit the chamber.

The first body portion 1068 is configured to expand into the gap 1076 toward the second body portion 1072 by receipt of the gas such that the size E of the gap 1076 is decreased. Specifically, the first body portion 1068 is configured to contour around each of the medical tubes 1014 as the first body portion 1068 expands towards the second body portion 1072. As such, the tube retainer 1030 is configured to retain the medical tubes 1014 of different sizes in the free flow state and the retention state.

In the free flow state (FIG. 10A), the size E of the gap is large enough such that the tube retainer 1030 is configured to enable movement of the medical tubes 1014 in the lateral direction B (in and out of the page, in FIG. 10A). In the free flow state, the second body portion 1072 resists movement of the medical tubes 1014 in the vertical direction C. When gas is pumped into the chamber of the first body portion 1068, the medical tubes 1014 within the gap 1076 are sandwiched between the first body portion 1068 and the second body portion 1072 such that the tube retainer 1030 is configured to resist movement in the longitudinal, lateral, and vertical directions A, B, C, thereby adjusting the tube retainer 1030 into the retention state (FIG. 10B).

In some embodiments, the second body portion 1072 is substantially parallel to the first body portion 1068 in the free flow state and the retention state. In other embodiments, the second body portion 1072 may be positioned at an angle relative to the first body portion 1068 such that the second body portion 1072 may be further adapted to move towards the first body portion 1068 by use of a threaded fastener extending from the second body portion 1072 and received in a threaded receptacle of the first body portion 1068 and a rotatable nut (not shown) positioned on the fastener. In some embodiments, the second body portion 1072 is rotated along a longitudinal axis (extending in the direction A) while positioned in the horizontal direction (e.g., in the position illustrated in FIG. 10A), such that an edge of the second body portion 1072 is rotated downwards to push the tubes the first body portion 1068 to change to the retention state from the free flow state. As such, the size E may be further altered for adjusting the tube retainer 1030 between the free flow state and the retention state. Specifically, the movement of the medical tube 104 may be restricted along the lateral direction B.

Figure 11:
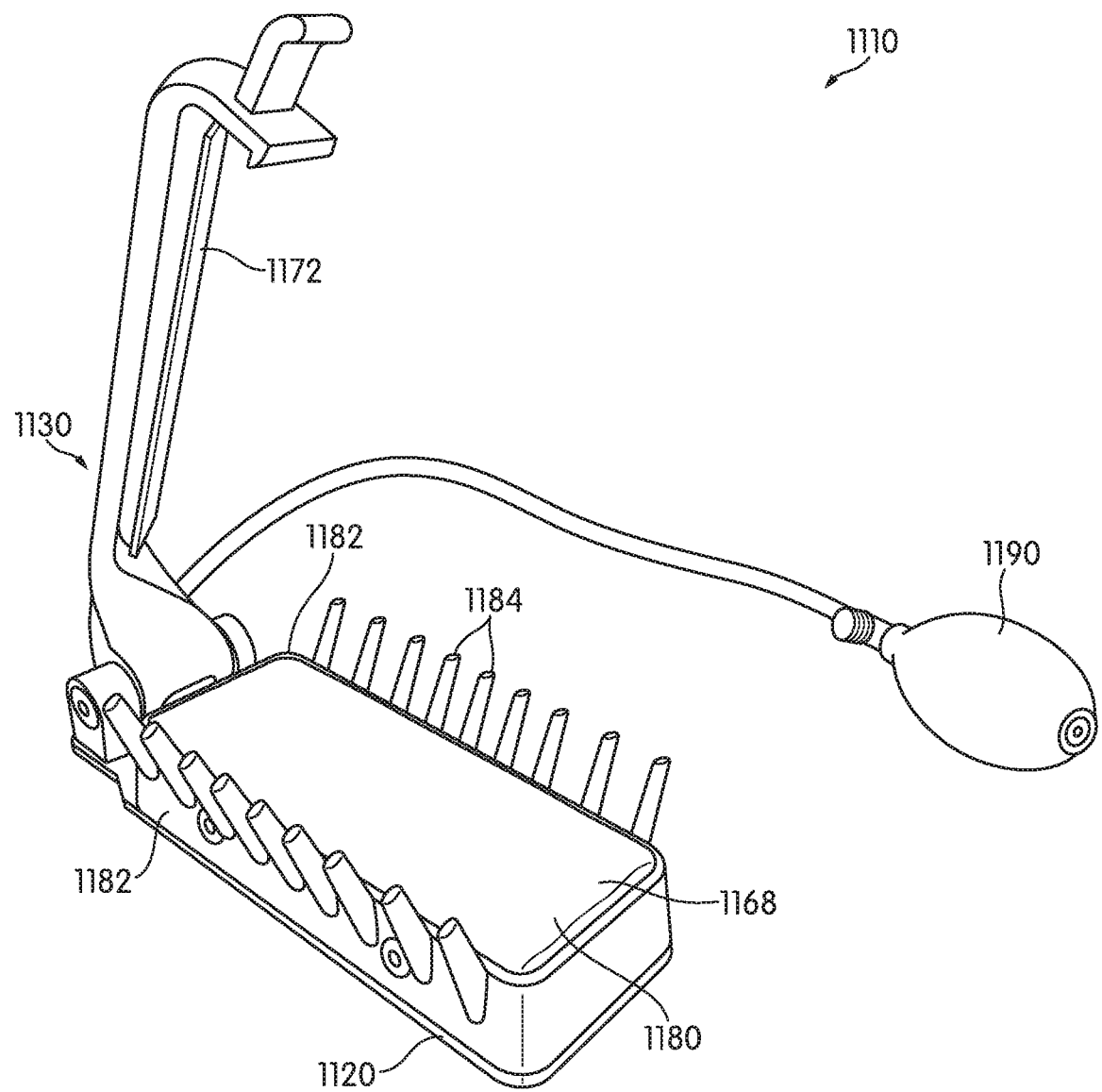
FIG. 11 is a perspective view of a medical tubing organizer according to an eleventh embodiment, the medical tubing organizer in the open state.

With reference to FIG. 11, the tube retainer 1130 includes first and second body portions 1168, 1172 similar to the tube retainer 1030 of FIGS. 10A-10B. The first body portion 1168 defines a chamber 1180 configured to receive the gas. The second body portion 1172 is rotatably coupled to the first body portion 1168 for adjusting the tube retainer 1130 between the open state (FIG. 11) and the free flow state (not shown). The first body portion 1168 further includes fingers 1184 extending from sides 1182 of the first body portion 1168 relative to the vertical direction C. The fingers 1184 are configured to separate the medical tubes (not shown) when the tube retainer 1130 is in the different states. For example, when the tube retainer 1130 is in the open state, the medical tubes may be positioned on the first body portion 1168 between the fingers 1184. When the second body portion 1172 is rotated to generally parallel to the first body portion 1168, the tube retainer 1130 is in the free flow state. Specifically, the medical tubes are allowed to move along the lateral direction B between each of the fingers 1184 within a gap (not shown) defined between the first body portion 1168 and the second body portion 1172. The first body portion 1168 is configured to expand into the gap toward the second body portion 1172 by receipt of the gas similar to the tube retainer 1030. As such, the medical tube within the gap is sandwiched between the first body portion 1168 and the second body portion 1172 such that the tube retainer 1130 is configured to resist movement in the longitudinal, lateral, and vertical directions A, B, C, thereby adjusting the tube retainer 1130 into the retention state.

With continued reference to FIG. 11, the tube retainer 1130 may further include a pump 1190 in fluid communication with the chamber 1180. The pump 1190 may be manually manipulated (e.g., squeezing by a hand) for pumping air into the chamber 1080. A release valve is also provided adjacent the pump 1190 to allow the gas to exit the chamber 1180.

Figure 12A:
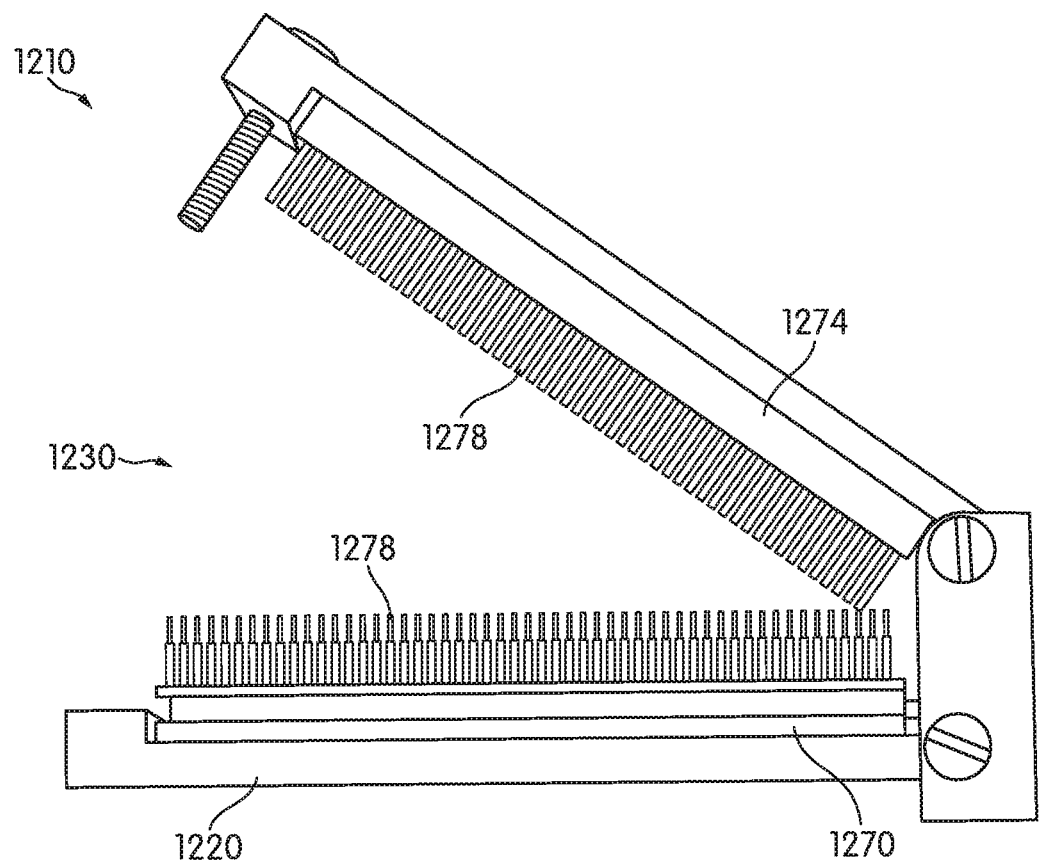
FIG. 12A is a side view of a medical tubing organizer according to a twelfth embodiment, the medical tubing organizer in the open state.
Figure 12B:
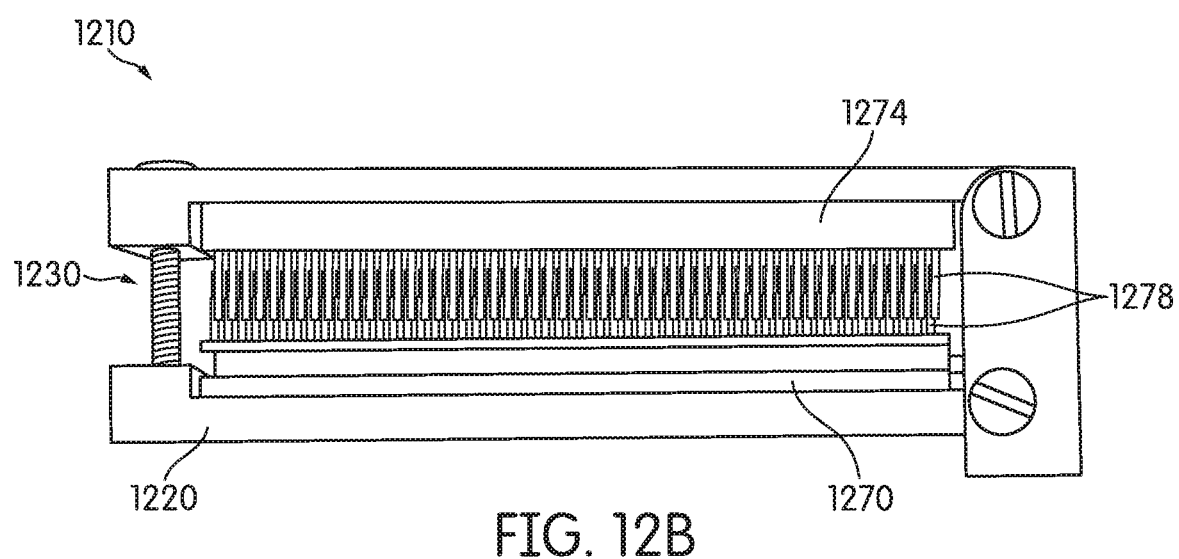
FIG. 12B is another side view of the medical tubing organizer of FIG. 12A in the retention state.

With reference to FIGS. 12A-12B, the tube retainer 1230 includes a first portion 1270 and a second portion 1274 rotatably coupled to the first portion 1270. The first and second portions 1270, 1274 each include finger members 1278 extending towards each other. The finger members 1278 are formed by flexible material, such as rubber. Furthermore, the finger members 1278 of the first portion 1270 are configured to receive a medical tube (not shown), such as the medical tube 14. The finger members 1278 are spaced along the longitudinal direction A such that the tube retainer 1230 is configured to retain the medical tubes of different sizes in the free flow state and the retention state. Rotation of the second portion 1274 relative to the first portion 1270 adjusts the tube retainer 1230 between the open state (FIG. 12A) and the retention state (FIG. 12B). Specifically, the finger members 1278 of the first and second portions 1270, 1274 are configured to resist movement in the longitudinal, lateral, and vertical directions A, B, C thereby adjusting the tube retainer 1230 into the retention state. In some embodiments, by only loosely coupling the non-hinged end of the second portion 1274 to the first portion 1270 (e.g., by only slightly engaging a threaded fastener of the second portion 1274 to a threaded receptacle of the first portion 1270), the tube retainer 1230 enters a free flow state. In the free flow state, the tube retainer 1230 is configured to resist movement in the longitudinal and vertical directions A, C, while the tubes are allowed to move along the lateral direction B.

While several embodiments described above have been described as having two discrete free flow and retention states, in some embodiments, further free flow and retention states are provided. For example, with reference to FIGS. 4A-C, the knob 492 is rotatable to provide further granularity offering varying levels of retention and flow of the medical tubes 414. In other words, the gap 464 decreases and increases continuously between states during adjustment and can be secured in any or a plurality of the positions along the continuum, rather than adjusting from the free-flow state to the retention state in one step. In some embodiments, similar continuous-style adjustment is provided with respect to the medical tube organizers of FIGS. 1A-12B. Accordingly, in some embodiments, a level of the retention of the medical tube 14 may be varied such that the tube retainer 30 allows movement of the medical tube 14 in at least one way (i.e., uni-directional) (e.g., relative to the lateral direction B, etc.) when in the retention state. In other embodiments, the medical tube organizers of FIGS. 1A-12B are configured to step between discrete states (e.g., the medical tube organizer 800 of FIGS. 8A-B) without being configured to be secured at intermediate states.

Figure 13A:
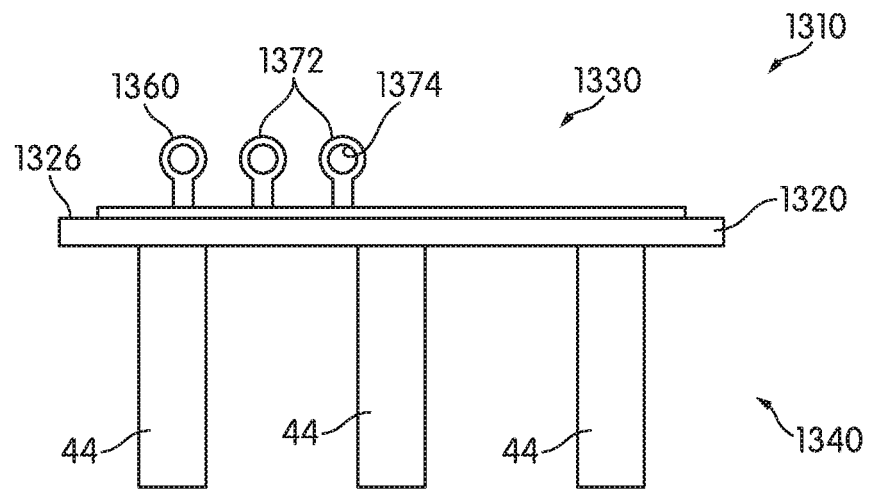
FIG. 13A is a side view of a medical tubing organizer according to a thirteenth embodiment, the medical tubing organizer including a base and projections extending from the base.
Figure 13B:
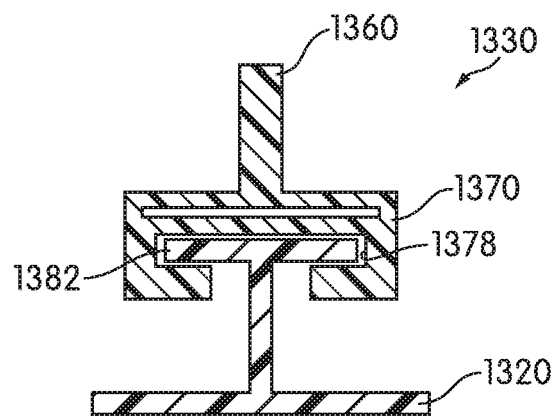
FIG. 13B is a cross sectional view of the base and one of the projections of FIG. 13A slidably coupled to the base.

With reference to FIGS. 13A-13B, 14A, 15A-15B, and 16A-16B, each of the plurality of projections 1360, 1460, 1560, 1660 forms a cylindrical body 1372, 1472, 1572, 1672 extending from the top 1326, 1426, 1526, 1626 of the base 1320, 1420, 1520, 1620 along the vertical direction C. Each cylindrical body 1372, 1472, 1572, 1672 may include one or more windows 1374, 1474, 1574, 1674 configured to receive the medical tube 14, 1514, 1614. The illustrated projections 1360, 1560, 1660 are detachably coupled to the base 1320, 1520, 1620. For example, as shown in FIGS. 13A-13B, each projection 1360 can be added and removed from the base 1320. In some embodiments, the projections 1460, 1560, 1660 are similarly detachably coupled to the base 1420, 1520, 1620. Accordingly, the number of medical tubes retained and organized by each medical tube organizer 1310, 1410, 1510, 1610 can be selectively modified by an end user.

Figure 14A:
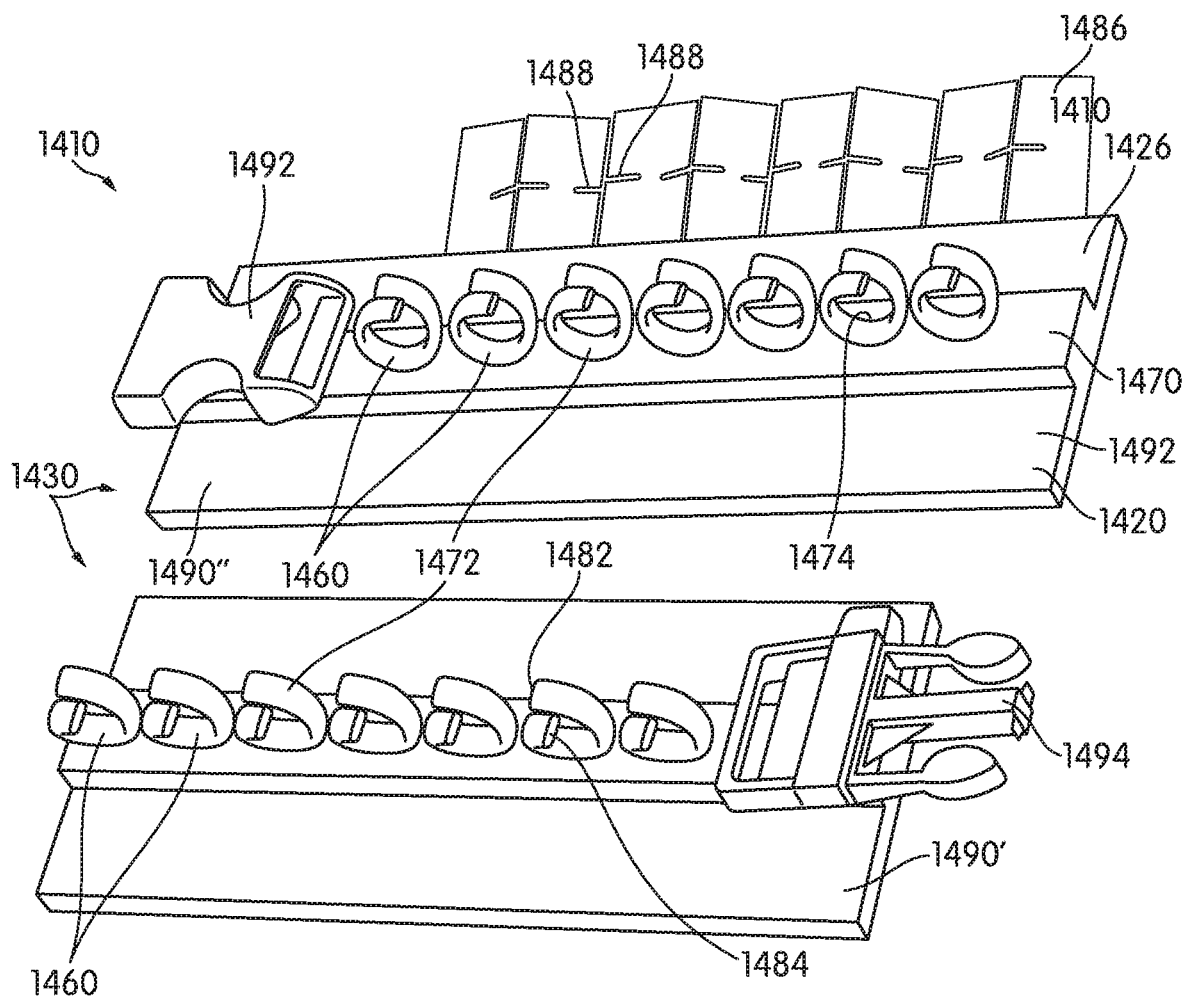
FIG. 14A is a front perspective view of a medical tubing organizer according to a fourteenth embodiment, the medical tubing organizer including first and second portions configured to couple together.
Figure 14B:
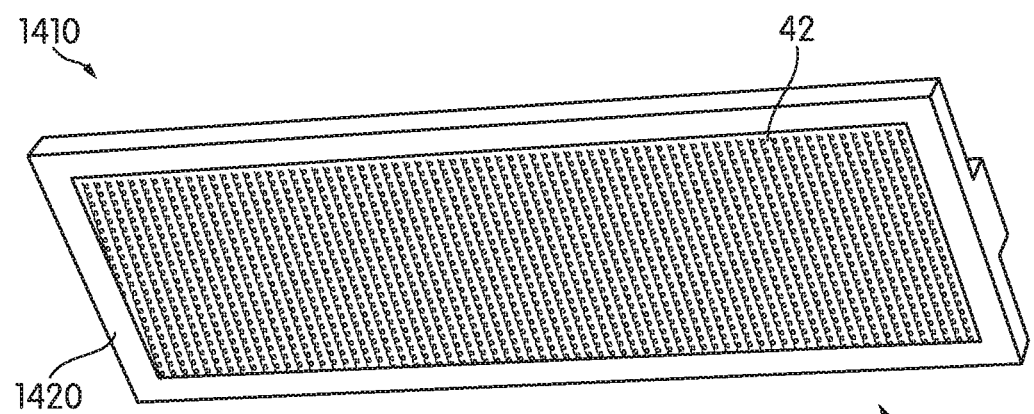
FIG. 14B is a back perspective view of the medical tubing organizer of FIG. 14A illustrating a hook and loop fastener positioned on a bottom of the medical tubing organizer.
Figure 15A:
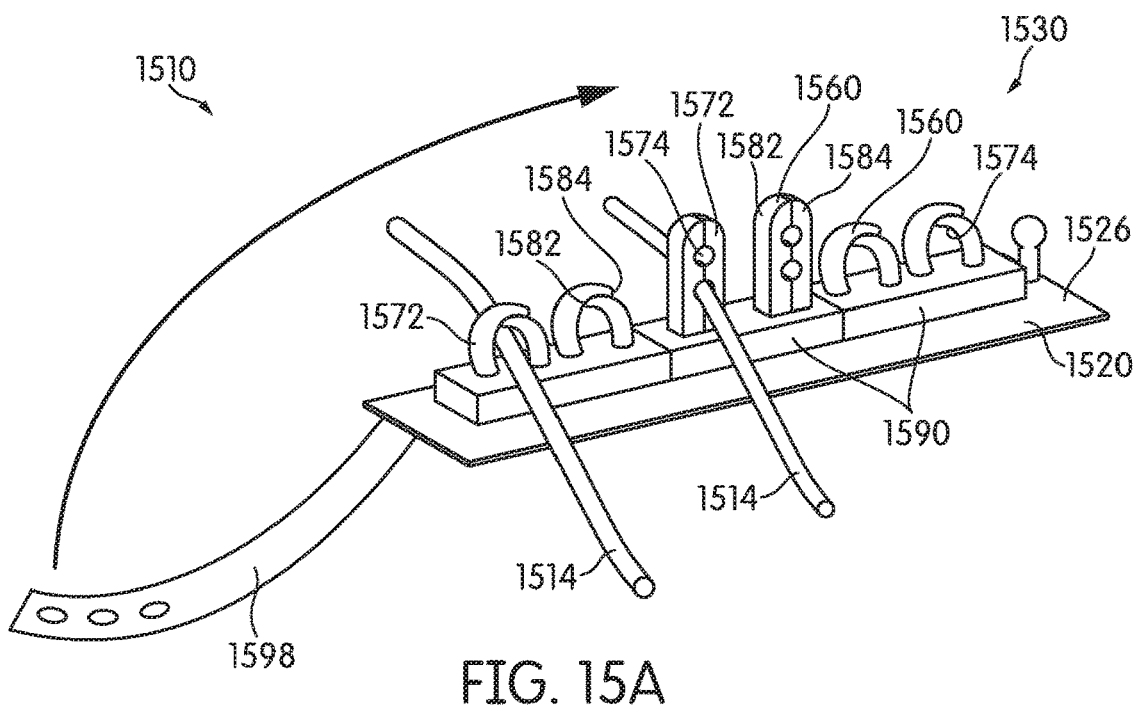
FIG. 15A is a front perspective view of a medical tubing organizer according to a fifteenth embodiment, the medical tubing organizer including a base, three portions coupled together and attached to the base, projections extending from the portions, and a cover extending from a side of the base.
Figure 15B:
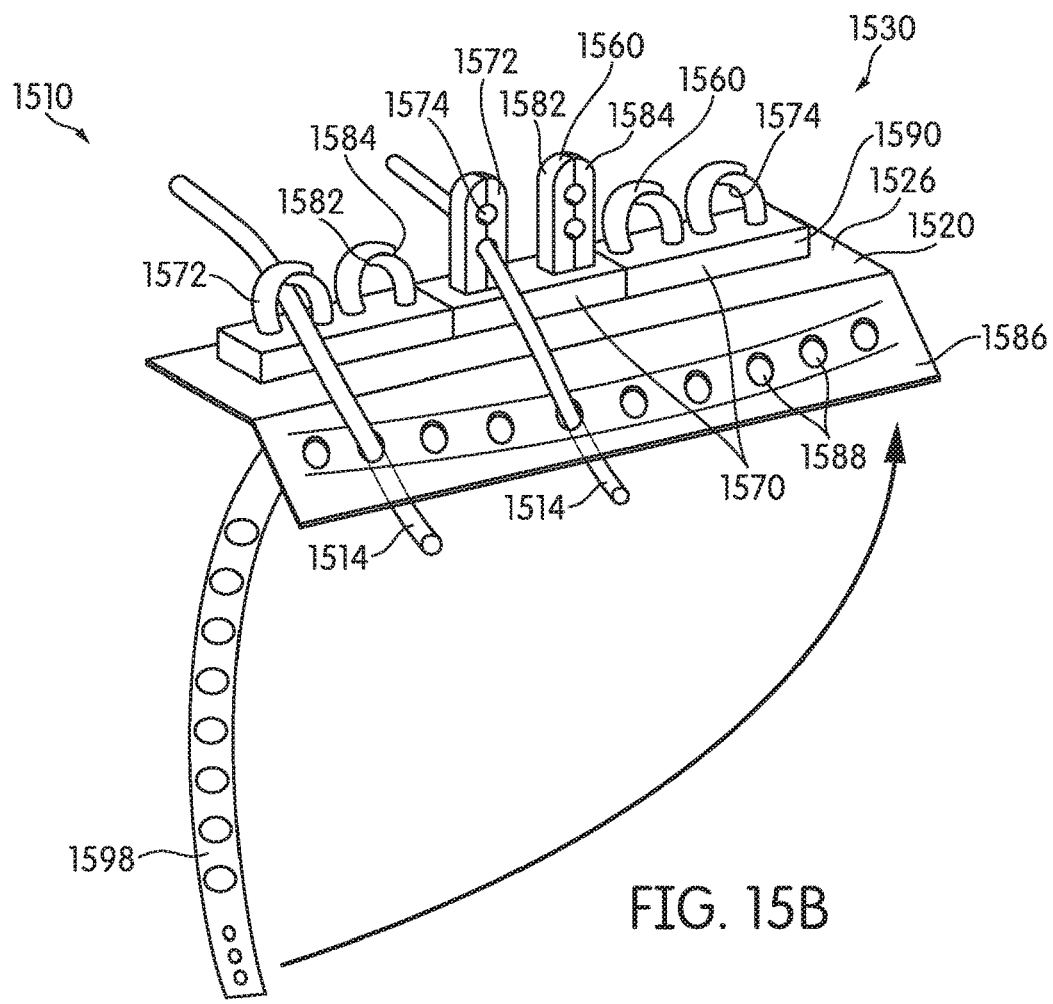
FIG. 15B is a front perspective view of another construction of the medical tubing organizer of FIG. 15A including a member extending from another side of the base, and the cover extending from the member.

With reference to FIGS. 13A-13B, 14A, 15A-15B, and 16A-16B, the tube retainer 1330, 1430, 1530, 1630 includes a foot portion 1370, 1470, 1570, 1670. In some embodiments, the foot portion 1370, 1570, 1670 is configured to detachably couple the tube retainer 1330, 1530, 1630 to the base. In some embodiments, each projection 1360, 1660 includes the foot portion 1370, 1670 (FIGS. 13A-13B and 16A-16B). In other embodiments, each group of projections 1560 includes the foot portion 1570 (FIGS. 15A-15B). However, in these embodiments, the number of projections per foot portion varies. Additionally, as shown in FIGS. 15A-15B, some of the projections 1560 include two or more windows 1574 (see, e.g., the two middle projections 1560 in FIGS. 15A-B). In some embodiments, at least some of the projections 1360, 1460, 1660 are similarly provided with two or more windows 1374, 1474, 1674.

Figure 16A:
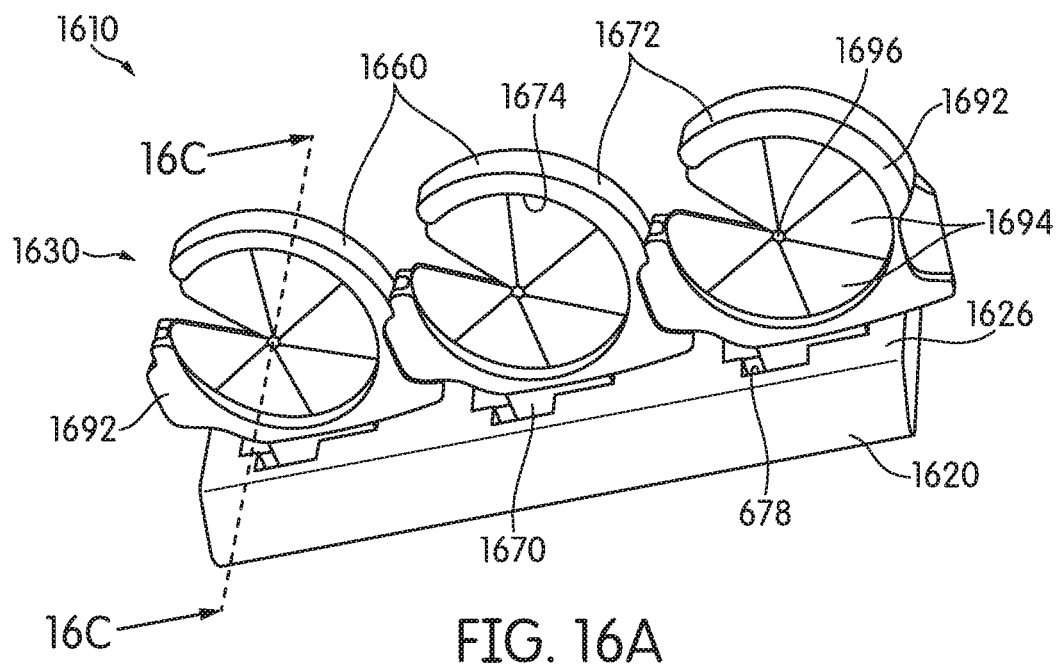
FIG. 16A is a front perspective view of a medical tubing organizer according to a sixteenth embodiment, the medical tubing organizer including a base, three projections coupled to the base, the projections configured to operate as one-way valves.
Figure 16B:
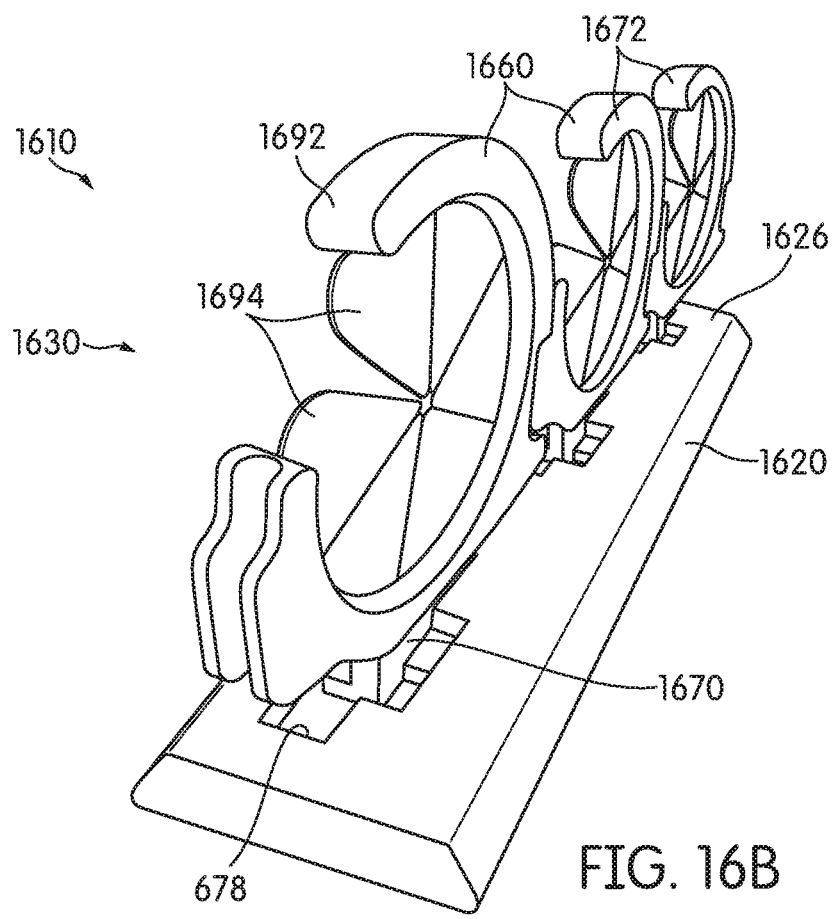
FIG. 16B is a side perspective view of the medical tubing organizer of FIG. 16A.

With reference to FIGS. 13A-13B and 16A-16B, the base 1320, 1620 is configured to receive each foot portion 1370, 1670. For example as shown in FIGS. 13A-13B, the foot portion 1370 forms a channel 1378 opposite the cylindrical body 1372 of the projection 1360. The base 1320 includes a track 1382 received within each channel 1378 for slidably attaching the plurality of projections 1360 to the base 1320. In other embodiments, as shown in FIGS. 16A-16B, the base 1620 includes a plurality of openings 1678 in which each opening 1678 is configured to receive one of the foot portions 1670. Specifically, the illustrated foot portion 1670 has an I-shape cross section configured to slide along the longitudinal direction A to secure each projection 1660 within the opening 1678 using the foot portion 1670.

With reference to FIGS. 14A and 15A-15B, in some embodiments, the tube retainer 1430, 1530 includes a plurality of portions 1490, 1590 detachably coupled. Each portion 1490, 1590 includes one or more projections 1460, 1560 for adjusting the quantity of the projections 1460, 1560. Specifically, each portion 1490, 1590 may be a portion of the base 1492 (FIG. 14A) or one of the foot portions 1570 (FIGS. 15A-15B). Furthermore, as shown in FIG. 14A, one of the portions 1490' may include a male connector 1494 and another of the portions 1490" may include a female connector 1496 for detachably coupling the portions 1490 together.

With continued reference to FIGS. 14A and 15A-15B, each projection 1460, 1560 includes the cylindrical body 1472, 1572 that has a first end 1482, 1582 and a second end 1484, 1584. The first and second ends 1482, 1582, 1484, 1584 of some of the projections 1460, 1560 overlap to form the window 1474, 1574. Conversely, the first and second ends 1482, 1582, 1484, 1584 of some of the projections 1460, 1560 are adjacent and abut each other to form the window 1474, 1574 (see, e.g., the middle two projection 1560 of FIG. 15A). The projections 1460, 1560 are formed by the flexible material, such as rubber, that are biased to an overlapping or abutting state to form the windows 1474, 1574 (as shown in FIGS. 14A, 15A, 15B). To insert a medical tube (e.g., the medical tube 1514), the first and second ends 1482, 1582, 1484, 1584 are pulled apart to provide entry into the windows 1474, 1574, and then the medical tube is inserted through the formed entries. Thus, the first and second ends 1482, 1582, 1484, 1584 are movable for positioning the medical tubes within each projection 1460, 1560.

With reference to FIGS. 14A and 15B, in some embodiments, the tube retainer 1430, 1530 includes a member 1486, 1586 extending from the base 1420, 1520. The illustrated member 1486, 1586 extends from a side of the base 1420, 1520 along the lateral direction B. The member 1486, 1586 includes a plurality of notches 1488, 1588 in which each notch 1488, 1588 is configured to receive the medical tube 1514 for resisting lateral movement of the medical tube 1514. The tube retainers 1330, 1430, and 1530 further resist vertical and longitudinal movement of received medical tubes. In other embodiments, the member 1586 forms concave depressions in a top surface of the member 1586. The concave depressions are configured to receive the medical tubes 1514 within each depression. Another member, such as a cover 1598 as described below may extend over the medical tubes 1514 in each depression for resisting movement of the medical tubes 1514 in the lateral and vertical directions B, C.

With reference to FIGS. 15A-15B, the tube retainer 1530 further includes the cover 1598. The cover 1598 may extend from the base 1520 (FIG. 15A) or the cover 1598 may extend from the member 1586. The cover 1598 is formed by the flexible material such as cloth. Furthermore, the cover 1598 is rotatably coupled to the base 1520 or member 1586 such that the cover 1598 may be positioned to resist movement of the medical tube 1514 in the any of the longitudinal, lateral, and vertical directions A, B, C. For example, in FIG. 15A, the cover 1598 can be positioned over the projections 1560 for resisting movement of the medical tube 1514 along the vertical direction C. In FIG. 15B, the cover 1598 can be positioned over the medical tube 1514 in one of the notches 1588 defined by the member 1586 for resisting movement of the medical tube 1514 in all of the directions A, B, C. In other words, the cover 1598 sandwiches the medical tubes 1514 between the cover 1598 and the member 1586 to resist movement.

Figure 16C:
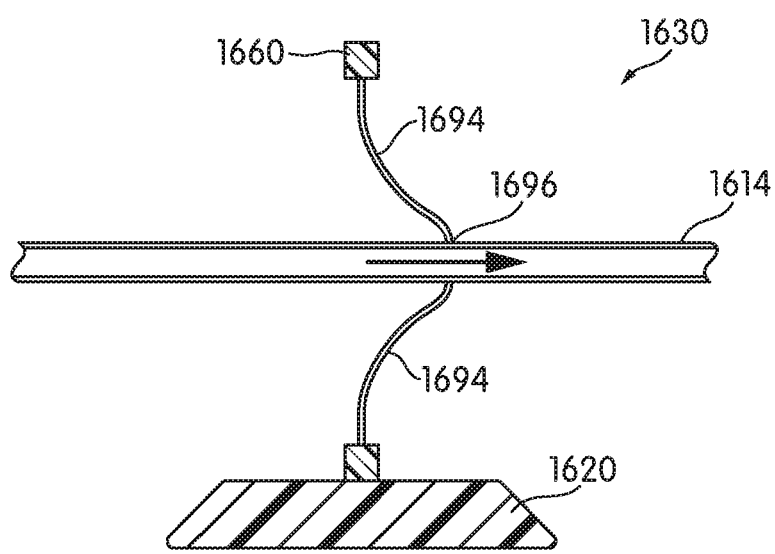
FIG. 16C is a cross sectional view of the medical tubing organizer viewed along section 16C-16C of FIG. 16A.

With reference to FIGS. 16A-16C, the cylindrical body 1672 of each projection 1660 forms a one-way valve 1692. The illustrated one-way valves 1692 include flexible portions 1694 positioned within each cylindrical body 1672 and extend to a center 1696 of the body 1670. The medical tubes 1614 (FIG. 16C) are positioned within each center 1696 such that the movement of the medical tube 1614 is allowed in one way along a direction and resisted in a second way substantially opposite the first way. As such, the projections 1660 are adapted to allow selective movement of the medical tube 1614. As shown in FIG. 16C, each projection 1660 is adapted to allow movement of the medical tube 1614 in a first way relative to the lateral direction B (in the direction of the arrow), and adapted to resist movement in a second way opposite the first way. Generally speaking, the direction of allowed lateral movement of the medical tube 1614 is toward the patient to which the medical tube 1614 is attached. Accordingly, a patient is provided the ability to pull the medical tube 1614 (e.g., when shifting position in a bed), while a tug on the medical tube 1614 in the opposite direction will be resisted by the one-way valve 1692, thereby lessening the likelihood that a medical tube 1614 will be unintentionally removed from the patient.

Although the one-way valves 1692 have been described with reference to the tube retainer 1630, any of the other embodiments above may be provided with the one-way valves 1692. For example, with reference to FIG. 1A, the projections 60 of one of the first and second portions 174, 178 may include flexible portions extending from the projections 60 along the longitudinal direction A, similar to the flexible portions 1694, such that the projections 60 form one-way valves. Specifically, only one side has the flexible portions such that the projections 60 allow movement of the medical tube 14 in one way relative to the lateral direction B, and resists movement in the opposite way.

As previously described, FIG. 17 illustrates the pad 50 coupled to the structure 18 via the connector 40 (e.g., strap 44). The pad 50 further includes the fastener 42 for attaching the pad 50 to a hook and loop fastener on the bottom side 28 of the base 20. In other embodiments, the pad 50 may include other connectors 40 as described above. Furthermore, the pad 50 may be attached to the base 20 using an adhesive. The structure 18 may be a limb (e.g., arm) of a patient such that the medical tubing organizer 10 may be positioned on the patient.

Although a connector may not have been discussed with respect to each embodiment above, a connector is provided on each of the various medical tube organizers described above, at least in some embodiments, to secure the medical tube organizers to the structure 18. The connector may be attached to one of the sides of the bases (e.g., of the base 120, 220, etc.) of these medical tube organizers and may be formed by one or more straps (see the connector 40, FIG. 1A, a hook and loop fastener for engaging a hook and loop fastener on the structure 18 (see the connector 1440, FIG. 14B)), adhesive, suction cups or the like.

Accordingly, various embodiments of a medical tubing organizer are described herein that enable the retention and organization of medical tubes. Although the disclosure has been described in detail with reference to certain embodiments, variations and modifications exist within the scope and spirit of one or more independent aspects of the disclosure as described. Various features and advantages of the disclosure are set forth in the following claims.

What is claimed is:

1. A medical tubing organizer comprising:
a base defining a longitudinal direction, a lateral direction being defined as substantially orthogonal to the longitudinal direction, and a vertical direction being defined as substantially orthogonal to the longitudinal and lateral directions;
a tube retainer positioned on a top of the base and configured to receive a medical tube that extends along the lateral direction, the tube retainer including a plurality of projections, each projection having a connected end and a free end, wherein the free ends are movable relative to each other, the tube retainer further configured to adjust between a free flow state and a retention state,
wherein, in the free flow state, the tube retainer is configured to enable movement of the medical tube in the lateral direction and resist movement in the longitudinal direction,
wherein, in the retention state, the tube retainer is configured to resist movement in the lateral, longitudinal, and vertical directions, and
wherein, when the tube retainer is in the retention state, the free end of at least one of the plurality of projections contacts the free end of an adjacent one of the plurality of projections;
an elongated member movably coupled to the base, wherein the tube retainer adjusts between the free flow state and the retention state by movement of the elongated member relative to the plurality of projections; and
a connector positioned on the base for selectively coupling the medical tubing organizer to a structure.

2. The medical tubing organizer of claim 1, wherein a the plurality of projections are movably coupled to the top of the base, the projections configured to move relative to the base for adjusting between the free flow state and the retention state.

3. The medical tubing organizer of claim 2, wherein the plurality of projections define gaps between adjacent projections, each gap configured to receive the medical tube, and wherein the tube retainer is adjustable between the free flow state and the retention state when the adjacent projections move relative to one another to alter the gaps.

4. The medical tubing organizer of claim 3, wherein the tube retainer is in the free flow state when the gaps between adjacent projections are at a first size, and wherein the tube retainer is in the retention state when the gaps between projections are at a second size narrower than the first size.

5. The medical tubing organizer of claim 3, wherein, while in the free flow state, a first gap of the gaps has a first size to accommodate the medical tube and a second gap of the gaps has a second size that is different than the first size to accommodate a second medical tube that is a different size than the medical tube.

6. The medical tubing organizer of claim 1, wherein the connector includes at least one selected from the group of a hook and loop fastener and a strap, the connector configured to detachably couple to the structure.

7. The medical tubing organizer of claim 1, further comprising:
a gap between the at least one of the plurality of projections and the adjacent one of the plurality of projections, the gap configured to receive the medical tube,
wherein, when the tube retainer is in the retention state, the elongated member extends in the longitudinal direction from a first end of the base over the gap and the top of the base.

8. The medical tubing organizer of claim 7, wherein the base and the tube retainer are arranged such that, when the connector couples the medical tubing organizer to the structure and the tube retainer is in the retention state, the tube retainer is positioned between the structure and the medical tube.

9. The medical tubing organizer of claim 8,
wherein the base includes a bottom side that is opposite the top, and
wherein, when the tube retainer is in a free flow state and the connector couples the medical tubing organizer to the structure, the gap opens in an outward facing direction away from the structure and the bottom side.

10. The medical tubing organizer of claim 8,
wherein the base includes a bottom side that is opposite the top, and
wherein, when the connector couples the medical tubing organizer to the structure, the bottom side is structure-facing and the free ends are projecting outward away from the structure and the bottom side.

11. The medical tubing organizer of claim 1, further comprising:
a gap between the at least one of the plurality of projections and the adjacent one of the plurality of projections, the gap configured to receive the medical tube,
wherein the retention state is one a plurality of retention states of the tube retainer, and each retention state is associated with a respective level of resistance to lateral movement of the medical tube, and
wherein the tube retainer adjusts between the free flow and the plurality of retention states based on an amount of movement of the elongated member relative to the plurality of projections.

12. The medical tubing organizer of claim 1, wherein each of the plurality of projections has an elongated shape extending away from the base such that each projection has a height in the vertical direction that is greater than a width in the longitudinal direction.

13. A method for organizing medical tubes including a base having a tube retainer and defining a longitudinal direction, the method comprising:
coupling, by a connector, the base to a structure;
receiving a medical tube in the tube retainer; and
adjusting, by the tube retainer, between a free flow state and a retention state in response to movement of an elongated member that is moveably coupled to the base, the tube retainer including a plurality of projections, each projection having a connected end and a free end, and wherein the free ends are movable relative to each other,
wherein, in the free flow state, the tube retainer allows movement of the medical tube in a lateral direction that is substantially orthogonal to the longitudinal direction, and resists movement of the medical tube in a vertical direction that is substantially orthogonal to the longitudinal and lateral directions,
wherein, in the retention state,
the tube retainer resists movement of the medical tube in the lateral and vertical directions, and the elongated member causes application of a compression force to the plurality of projections such that the free end of at least one of the plurality of projections contacts the free end of an adjacent one of the plurality of projections.

14. The method of claim 13, wherein the plurality of projections are movably coupled to the base, the method further comprising moving at least one of the projections relative to another one of the projections for adjusting between the free flow state and the retention state.

15. The method of claim 14, wherein the tube retainer is in the free flow state when the at least one projection and the another one of the projections move away from each other along the longitudinal axis, and wherein the tube retainer is in the retention state when the at least one projection and the another one of the projections move towards each other along the longitudinal axis.

16. The method of claim 13, wherein the plurality of projections define gaps between adjacent projections, each gap configured to receive the medical tube, the method further comprising altering at least one of the gaps by moving at least one of the projections relative to another one of the projections for adjusting between the free flow state and the retention state.

17. The method of claim 16, wherein the tube retainer is in the free flow state when the gaps between adjacent projections are at a first size, and wherein the tube retainer is in the retention state when the gaps between projections are at a second size narrower than the first size.

18. The method of claim 13, further comprising:
a gap between the at least one of the plurality of projections and the adjacent one of the plurality of projections, the gap configured to receive the medical tube,
wherein the retention state is one a plurality of retention states of the tube retainer, and each retention state is associated with a respective level of resistance to lateral movement of the medical tube, and
wherein the tube retainer adjusts between the free flow and the plurality of retention states based on an amount of movement of the elongated member relative to the plurality of projections.

19. The method of claim 13, wherein each of the plurality of projections has an elongated shape extending away from the base such that each projection has a height in the vertical direction that is greater than a width in the longitudinal direction.

20. A medical tubing organizer comprising:
a base defining a longitudinal direction, a lateral direction being defined as substantially orthogonal to the longitudinal direction, and a vertical direction being defined as substantially orthogonal to the longitudinal and lateral directions;
a tube retainer positioned on the base and configured to receive a medical tube that extends along the lateral direction, the tube retainer including a plurality of projections, each projection having a connected end and a free end, the free ends of the projections configured to move relative to each other for adjusting the tube retainer between a free flow state and a plurality of retention states,
wherein, in the free flow state, the tube retainer is configured to enable movement of the medical tube in the lateral direction and resist movement in the longitudinal direction,
wherein, in the plurality of retention states, the tube retainer is configured to resist movement in the lateral, longitudinal, and vertical directions, and each retention state of the plurality of retention states is associated with a respective level of resistance to lateral movement of the medical tube,
wherein respective free ends of adjacent projections of the plurality of projections are configured to move closer together along the longitudinal direction and to contact one another to adjust from the free flow state to one of the plurality of retention states, and
wherein the respective free ends of the adjacent projections are configured to move further away from each other along the longitudinal direction to adjust from the one of the plurality of retention states to the free flow state;
a gap between the at least one of the plurality of projections and the adjacent one of the plurality of projections, the gap configured to receive the medical tube;
a strap coupled to the base, wherein the tube retainer adjusts between the free flow state and the plurality of retention states based on an amount of movement of the strap relative to the plurality of projections in the longitudinal direction; and
a connector positioned on the base for selectively coupling the medical tubing organizer to a structure, wherein the base and the tube retainer are arranged such that,
when the connector couples the medical tubing organizer to the structure and the tube retainer is in the retention state, the tube retainer is positioned between the structure and the medical tube, and
when the connector couples the medical tubing organizer to the structure and the tube retainer is in the free state, the gap opens in an outward facing direction away from the structure.

21. The medical tube organizer of claim 20, wherein the gap is a first gap of a plurality of gaps, wherein each gap is defined by a set of adjacent projections of the plurality of projections, and wherein each gap configured to receive the medical tube, and wherein the tube retainer is adjustable between the free flow state and the plurality of retention states when respective free ends of sets of the adjacent projections move relative to one another to alter the gaps.

22. The medical tubing organizer of claim 21, wherein the tube retainer is in the free flow state when the gaps between the sets of adjacent projections are at a first size, and wherein the tube retainer is in the one of the plurality of retention states when the gaps between projections are at a second size narrower than the first size.

23. The medical tubing organizer of claim 20, wherein each of the plurality of projections has an elongated shape extending away from the base such that each projection has a height in the vertical direction that is greater than a width in the longitudinal direction.

24. The medical tubing organizer of claim 20,
wherein respective free ends of adjacent projections of the plurality of projections have respective flat abutting surface portions to contact one another when in the one of the plurality of retention states, and
wherein adjacent projections of the plurality of projections have respective curved tube receiving surface portions spaced apart from one another when in the one of the plurality of retention states.

* * * * *